United States Patent
Daley

(10) Patent No.: US 6,777,415 B2
(45) Date of Patent: Aug. 17, 2004

(54) METHODS OF INDUCING CANCER CELL DEATH AND TUMOR REGRESSION

(76) Inventor: George Q. Daley, 50 Young Rd., Weston, MA (US) 02193

( * ) Notice: Subject to any disclaimer, the term of this patent is extended or adjusted under 35 U.S.C. 154(b) by 0 days.

(21) Appl. No.: 09/971,545

(22) Filed: Oct. 5, 2001

(65) Prior Publication Data

US 2002/0128280 A1 Sep. 12, 2002

Related U.S. Application Data

(60) Provisional application No. 60/238,240, filed on Oct. 5, 2000.

(51) Int. Cl.⁷ ..................... A61K 31/44; A61K 31/501
(52) U.S. Cl. ............................. 514/252.14; 514/252.18; 514/253.01; 514/290; 514/908; 514/922
(58) Field of Search ....................... 514/252.14, 252.18, 514/253.01, 290, 908, 922

(56) References Cited

U.S. PATENT DOCUMENTS

| | | | |
|---|---|---|---|
| 5,874,442 A | 2/1999 | Doll et al. | 514/290 |
| 6,096,757 A | 8/2000 | Bishop et al. | 514/290 |
| 6,316,462 B1 | 11/2001 | Bishop et al. | 514/290 |
| 6,465,448 B1 * | 10/2002 | Gerson et al. | 514/183 |
| 2002/0077301 A1 * | 6/2002 | Daley et al. | 514/27 |

FOREIGN PATENT DOCUMENTS

| | | | |
|---|---|---|---|
| WO | WO 92/11034 | | 7/1992 |
| WO | WO 97/36587 | | 10/1997 |
| WO | WO 97/45412 | | 12/1997 |
| WO | WO 98/57945 | | 12/1998 |
| WO | WO 98/57948 | | 12/1998 |
| WO | WO 00/42042 | | 7/2000 |
| WO | WO 00/61142 | * | 10/2000 |
| WO | WO 00/61145 | | 10/2000 |
| WO | WO 02/0024 A1 | * | 1/2002 |

OTHER PUBLICATIONS

Cox A.D. et al., "Farnesyltransferase inhibitors and Cancer Treatment: Targeting Simply Ras?" BBA—Reviews on Cancer, Elsevier Science BV, Amsterdam, NL, vol. 1333, No. 1, 1997 pp. F51–F71, XP000944880; ISSN: 0304–419X.

International Search Report dated Nov. 21, 2002 for International Application No. PCT/US01/42509.

* cited by examiner

Primary Examiner—Frederick Krass
(74) Attorney, Agent, or Firm—Henry C. Jeanette

(57) ABSTRACT

Methods are provided for treating cancer, comprising administering (1) a farnesyl protein transferase inhibitor in conjunction with (2) an additional Ras signaling pathway inhibitor to induce cancer cell death and tumor regression.

6 Claims, 1 Drawing Sheet

METHODS OF INDUCING CANCER CELL DEATH AND TUMOR REGRESSION

This application asserts the priority of U.S. provisional application serial No. 60/238,240 filed Oct. 5, 2000.

FIELD OF THE INVENTION

This invention describes novel methods of treating subjects afflicted with cancers, including tumors and metastatic disease. In particular, this invention provides methods of treating cancer comprising the combined use of (1) a farnesyl protein transferase ("FPT") inhibitor and (2) an additional Ras signaling pathway inhibitor to induce a synergistic level of cancer cell death (apoptotic cell death in particular), thus permitting low dose treatment regimens.

BACKGROUND OF THE INVENTION

FIG. 1 of the present specification shows a simplified linear depiction of a signal transduction pathway that leads to cellular proliferation. This pathway is referred to herein as the "Ras signaling pathway" because Ras is a central relay in this pathway, receiving signals from upstream elements (e.g., growth factor receptors) and transmitting them to downstream elements.

The signaling pathways initiated by growth factor receptors which lead to cellular proliferation, and in some cases malignant transformation, are being elucidated. Many growth factor receptors such as those for epidermal growth factor (EGF) and platelet-derived growth factor (PDGF), as well as EGF receptor-related molecules (e.g. Her-2/Neu/ErbB2), possess an intrinsic tyrosine kinase activity which is activated by ligand-induced receptor dimerization (Heldin, 1995). This results in autophosphorylation of the receptor on tyrosine residues and the binding of proteins containing Src-homology 2 (SH2) domains. Two such SH2 proteins are Grb2 and SHC which indirectly activate the plasma membrane-associated, small GTP-binding protein Ras. Ras activation also occurs in response to ligand binding to seven transmembrane domain G-protein coupled receptors (e.g. Gutkind, 1998). Activation of Ras and other growth factor receptor-regulated signaling pathways ultimately leads to changes in the cytoskeleton and gene expression which are necessary for cellular proliferation, differentiation, and transformation (reviewed in Campbell et al., 1998).

The 3 human ras genes (Ha-Ras, N-Ras, and Ki-Ras) encode 4 proteins (due to alternative splicing of the Ki-Ras mRNA). Under normal circumstances, Ras proteins cycle between an active (GTP-bound) state and an inactive (GDP-bound) state. Ras activation occurs by exchange of bound GDP for GTP, which is facilitated by a family of guanine nucleotide exchange factors. Ras inactivation occurs by hydrolysis of bound GTP to GDP. This reaction is facilitated by GTPase activating proteins (GAPs) (Trahey and McCormick, 1987). In many human cancers, Ras proteins become oncogenically activated by mutations which destroy their GTPase activity, and thus deregulate Ras signaling (reviewed in Campbell et al., 1998).

Multiple candidate Ras effectors exist that may serve downstream of Ras in signal transduction and oncogenic transformation, including members of the Rho family of small GTPases, phosphatidylinositol-3 kinase (PI3K) and the serine/threonine protein kinase c-Raf-1 (reviewed in Campbell et al., 1998). Raf-mediated signaling is the best characterized Ras effector pathway. Activated Ras recruits Raf to the membrane where Raf activation occurs. Activated Raf is the initial component of a kinase cascade, the Mitogen-Activated Protein Kinase (MAPK) cascade (reviewed in Lowy and Willumsen, 1993; Campbell et al., 1998). Raf phosphorylates and activates the MEK1and MEK2 (MAPK/ERK kinase) protein kinases which, in turn, phosphorylate and activate the Extracellular signal Regulated Kinases ERK1 and ERK2 (also known as MAPK1 and MAPK2). Unlike their downstream targets, ERK1,2, the MEK1,2 proteins are highly specific enzymes whose only known substrates are the ERK1,2 proteins. Upon activation, ERK1 and ERK2 phosphorylate (and thus regulate) a variety of target proteins, including nuclear transcription factors, leading to the ultimate cellular response. This linear pathway of Ras signaling is diagrammed in FIG. 1.

The importance of these signaling pathways in the abnormal growth of cancer cells is indicated by the finding that growth factor receptor and Ras pathway components are often mutated and/or overexpressed in cancer. For example, Ras is mutationally activated in about 30% of human cancers including a high percentage of major epithelial cancers such as lung, colon and pancreatic cancers. Additionally, overexpression of growth factor receptors occurs in a number of cancers (e.g. overexpression of the Her-2/Neu receptor occurs in about 30% of human breast cancer). These observations have led to the pursuit and development of agents designed to block individual components of either signal transduction pathway. While such agents hold potential as novel cancer therapeutics, many inhibitors of signal transduction are thought to act in a cytostatic rather than a cytotoxic fashion by blocking the cell's progression through the cell cycle. This distinguishes them from traditional cancer chemotherapy drugs in being less toxic but also possessing less dramatic antitumor activity.

Therefore, there remains a challenge to provide new and improved methods of treating cancer. For instance, to treat tumorigenic cancer cells, it would be highly desirable to provide new methods that achieve a dramatic and selective induction of cancer cell death while minimizing potential toxic side effects against normal, untransformed cells. The present invention provides just such methods of treatment.

SUMMARY OF THE INVENTION

The present invention provides methods of treating cancer in a patient (e.g., a mammal such as a human) in need of such treatment, comprising administering an effective amount of (1) a farnesyl protein transferase (FPT) inhibitor and (2) an additional Ras signaling pathway inhibitor. The methods of the present invention achieve an unexpectedly dramatic induction of cancer cell death (apoptotic cell death in particular). The effects are synergistic, and highly selective against transformed cells (particularly tumorigenic cancer cells), thus enabling the use of low doses to minimize potential toxic side effects against normal, untransformed cells. Moreover, the methods of the present invention were surprisingly found to have a long-lasting, sustained effect on blocking cell signaling, again while minimizing potential toxic side effects against normal, untransformed cells. None of these effects, let alone their magnitude, could have been predicted prior to the present invention. Furthermore, taking advantage of the surprising synergy and sustained, long-lasting effects of this invention, special-low dose methods are provided so that cancer cell death is effectively achieved while, at the same time, maintaining low risk of potential toxic side effects on normal, untransformed cells. The methods of the present invention are particularly useful for the treatment of various tumorigenic cancers, especially epithelial cancers, (e.g., pancreatic cancer, ovarian cancer, prostate cancer, lung cancer, breast cancer, colorectal cancer, and bladder cancer), and melanoma.

DETAILED DESCRIPTION OF THE INVENTION

Figure 1:
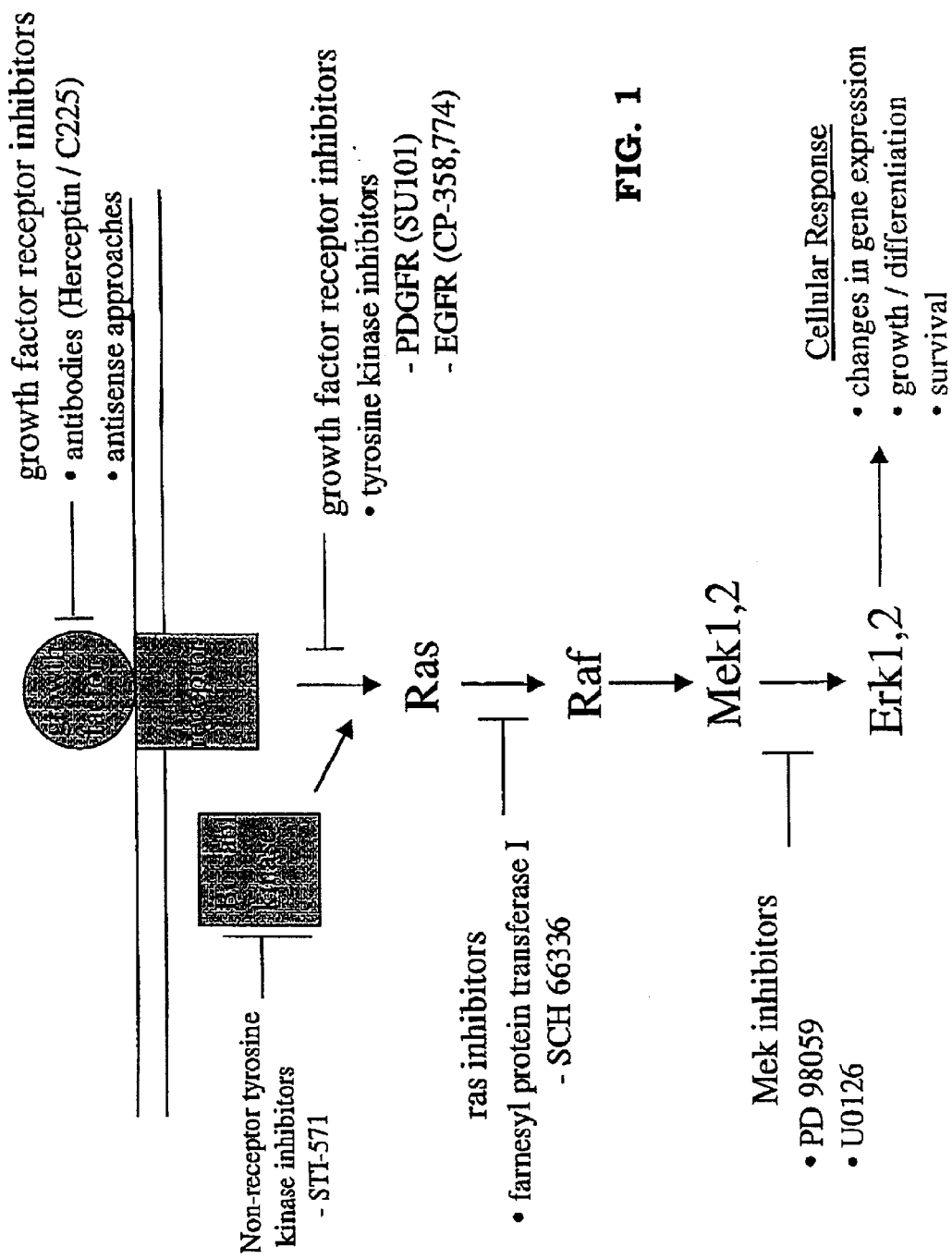
FIG. 1: Ras Signal Transduction: Schematic representation of the components of the RAS/MAPK signal transduction pathway. This linear pathway from growth factor receptor to ERK activation was the first Ras-mediated pathway to be elucidated. Also indicated are steps targeted by various inhibitors including the FPT inhibitor SCH 66336, the MEK inhibitors PDO98059 and U0126, and non-receptor tyrosine kinase inhibitor STI-571.

The present invention provides novel methods of treating cancer by combining (1) a farnesyl protein transferase (FPT) inhibitor, and (2) an additional Ras pathway signaling inhibitor.

(1) A "farnesyl protein transferase inhibitor" or "FPT inhibitor" or "FTI" is defined herein as a compound which: (i) potently inhibits FPT (but preferably not geranylgeranyl protein transferase I, in vitro); (ii) blocks the phenotypic change induced by a form of transforming H-ras which is a farnesyl acceptor (but preferably not by a form of transforming H-ras engineered to be a geranylgeranyl acceptor); (iii) blocks intracellular farnesylation of ras; and (iv) blocks abnormal cell growth.

(2) A "Ras signaling pathyway inhibitor" is defined herein as an agent that blocks the activity of any protein in the signal transduction pathway shown in FIG. 1. A particularly preferred Ras signaling pathway inhibitor is a "MEK inhibitor", which is defined herein as an agent that blocks the in vitro enzyme activity of a MEK (MAPK/ERK kinase) protein (preferably inhibiting MEK1 and MEK2), and thus blocks the activation of a MAPK protein as evidenced by a block in the phosphorylation of the MAPK protein. This can be detected by western blot analysis for phosphorylated MAPK as described in, e.g., Dudley et al., Proc Natl Acad Sci. 92:7686–7689 (1995), and Favata et al., J Bio Chem. 273:18623–32(1998).

1. FPT Inhibitors

As single agents, or in combination with chemotherapy (see, e.g., Liu et al., 1998), FPT inhibitors represent a leading approach for blocking the function of Ras oncoproeins. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors, most notably the tricyclic FPT inhibitors exemplified by SCH 66336. FPT inhibitors interfere with the post-translational processing of Ras proteins in cells and demonstrate antitumor activity in a wide variety of in vitro and in vivo cancer models (Bishop et al., 1995; Liu et al., 1998). The antitumor activity of SCH 66336 includes inhibition of anchorage-independent growth of a variety of human tumor cell lines in vitro and their growth as xenografts in immuno-compromised mice (Liu et al., 1998). Human tumor cell lines differ significantly in their sensitivity to the growth effects of FPT inhibitors. Sensitivity or resistance does not correlate with Ras mutational status.

In several transgenic mouse tumor models (e.g. MMTV-H-Ras, WAP-H-Ras, TGFα and TGFα/neu) significant tumor regressions are induced by treatment with FPT inhibitors. These regressions are associated with an increase in apoptosis (Liu et al 1998; Barrington et al., 1998; Norgaard et al., 1999). FPT inhibitors can also induce apoptosis of transformed cells in culture. The apoptotic effect in vitro has been reported to require growth in low serum or forced growth in suspension (Hung and Chaung, 1998: Lebowitz et al., 1997; Suzuki et al., 1998).

It has also been shown that FPT inhibitor treatment reduces the activity of the MAPK pathway in Ha-Ras-transformed Rat1 cells (e.g. James et al., 1994). This decrease in MAPK activity correlates with a decrease in cell growth. FPT inhibitors did not reduce MAPK activity in untransformed Rat1 cells.

A preferred FPT Inhibitory Compound referred to herein as "SCH 66336" is as follows:

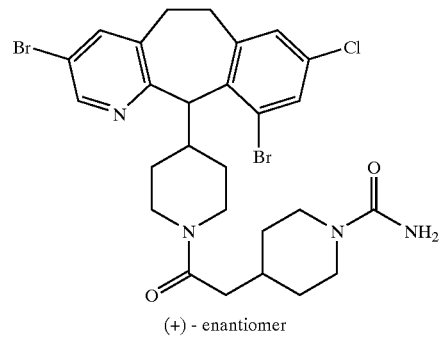

(+) - enantiomer

2. Agents Targeting MEK

The MAPK pathway has also been examined as a target for the development of anti-cancer therapeutics and the effects of specific inhibitors of this pathway on tumor cell lines have been described (Dudley et al., 1995; Favata et al., 1998). The best-characterized MEK inhibitor is PD098059, a small molecule that inhibits the activity of MEK1 and MEK2 via direct binding in a manner that is non-competitive with respect to either substrate (ATP or ERK protein). This results in decreased MEK1 and MEK2 phosphorylation and decreased activation of the MEK substrates, ERK1 and ERK2. PD098059 treatment blocks growth factor-mediated proliferation and anchorage-independent growth of Ras-transformed cells (Alessi et al., 1995, J Biol Chem. 270-27489–27494).

Recently, a novel MEK inhibitor, U0126, was reported which binds to MEK with higher affinity than PD098059 (Favata et al., 1998). For more detailed information on MEK inhibitors, and methods of preparing MEK inhibitors, reference can be made, e.g., to international patent publications WO 99/01421 (Jan. 14, 1999) and WO 99/01426 (Jan. 14, 1999).

3. Agents Targeting Growth Factor Receptors

Two primary approaches have been taken to block growth factor receptor signaling pathways: (i) monoclonal antibodies directed against the receptor; (ii) inhibitors of the receptor tyrosine kinase activity; and (iii) antisense nucleic acids to block protein expression. Anti-receptor monoclonal antibodies include those targeting the erbB2 receptor (e.g. Genentech's HERCEPTIN®/trastuzumab) and those targeting the EGF receptor. The best characterized anti-EGF receptor antibody is the chimeric antibody C225 (Goldstein et al. (1995), Clin Cancer Res. 1:1311–1318). Both HERCEPTIN® and C225 have demonstrated efficacy in preclinical tumor models in which their cognate receptors are expressed.

Small molecule inhibitors of tyrosine kinase activity have also been reported with at least two of these compounds already in human clinical trials: Sugen's PDGF receptor inhibitor, SU101, which is in phase III clinical trials for glioma and earlier stage trials for other cancer indications, and Pfizer's EGF receptor inhibitor, CP-358,774, which is in early phase clinical trials (Moyer et al. (1997), Cancer Res. 57: 4838–4848).

4. Agents Targeting Non-receptor Tyrosine Kinases

Another class of signal transduction inhibitors which show an added benefit when combined with farnesyl transferase inhibitors are inhibitors of non-receptor tyrosine kinases. Like receptor tyrosine kinases, non-receptor tyrosine kinases lie upstream in the Ras signal transduction pathway and lead to Ras activation. Unlike receptor tyrosine kinases, non-receptor tyrosine kinases are not localized to the cell membrane, but are soluble proteins localized to the cytoplasm. Examples of these include the src and abl tyrosine kinases. In nearly all patients with chronic myelogenous leukemia, the abl tyrosine kinase is deregulated (i.e. constitutively activated) by a chromosomal translocation in the malignant cells leading to production of the bcr-abl fusion protein.

Recently, small molecules which inhibit the kinase activity of the bcr-abl fusion protein have been developed and are currently in clinical trials. An example of this is STI571 (CGP57148), a 2-phenylaminopyrimidine derivative (See Buchdunger et al (1996). Cancer Research 56: 100–104; Druker et al (1996) Nature Medicine 2: 561–566; Weisberg & Griffin (2000) Blood 95: 3498–3505). STI 571 has the following structure:

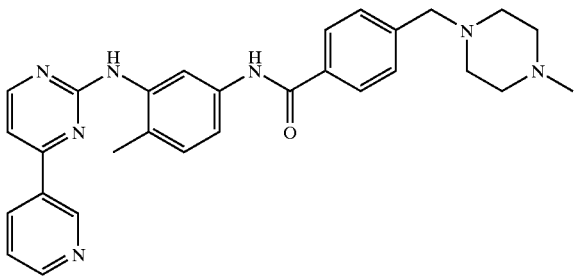

Recent studies surprisingly indicate that the combination of the farnesyl transferase inhibitor SCH 66336 with STI571 results in enhanced activity against bcr-abl transformed cells, greater than that seen with either single agent alone.

5. Other Signaling Antagonists

In addition to the approaches described above, other elements of the Ras signaling pathway and other signal transduction pathways have been targeted for cancer drug discovery. The SH2 proteins (SHC and Grb2), which link growth factor receptors to Ras activation, have been targeted by peptidomimetic agents that block the binding of SH2 domains to phosphotyrosine-containing protein sequences.

The protein kinase Raf, which links Ras to MEK1,2 activation, has also been targeted both by small molecule kinase inhibitors and by antisense approaches. The latter approach (ISIS-5132) is in phase II clinical trials (Monia et al., 1996).

Other relevant intracellular signaling targets include the phospho-lipid kinase PI3K (phosphatidylinositol-3 kinase) and protein kinase C.

In preferred embodiments, the methods of the present invention can be used to treat tumorigenic cancer cells by having a significant effect on cell death (e.g. by apoptosis) in the case of the cancerous cells (i.e., having a significant effect on cell death beyond mere arrest of growth) while, at the same time, the active agents can be administered in relatively low doses (and/or less frequently) to minimize potential toxic side effects against normal, untransformed cells. In addition, the present invention provides new methods of treating cancer by providing a longer, more sustained effect on blocking cell signaling, while, at the same time, minimizing the risk of potential toxic side effects against normal cells.

Thus, the present invention also provides methods of inducing a synergistic level of cancer cell death (e.g. apoptosis) in a cancer patient, comprising administering, concurrently or sequentially, effective amounts of (1) a FPT inhibitor and (2) an additional Ras signaling pathway inhibitor (i.e., in amounts sufficient to induce a synergistic level of cancer death as measured, e.g., by the propidium iodide fluorescence assay described in Dengler et al., (1995) Anticancer Drugs. 6:522–32. Similarly, methods are provided herein for killing cancer cells in a cancer patient (as measured by the assay of Dengler et al 1995) comprising administering effective amount of (1) a FPT inhibitor and (2) an additional Ras signaling pathway inhibitor.

Furthermore, in preferred embodiments, the methods of the present invention include methods for treating tumors and regressing tumor volume (e.g., as measured by CAT scan) in a patient in need of such treatment (e.g., a mammal such as a human) by administering, concurrently or sequentially, (1) an FPT inhibitor and (2) an additional Ras signaling pathway inhibitor in amounts sufficient to achieve. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, colon cancers (e.g., colorectal carcinomas, such as, for example, colon adenocarcinoma and colon adenoma), ovarian cancer, bladder carcinoma, and cancers of the liver. Other cancers that can be treated include melanoma, myeloid leukemias (for example, acute myelogenous leukemia), sarcomas, thyroid follicular cancer, and myelodysplastic syndrome.

Pharmaceutical compositions comprising an FPT inhibitor and an additional Ras signaling pathway inhibitor, for the treatment of cancer (including induction of cancer cell death and tumor regression), and preparation of such compositions, are also provided by the present invention.

As used herein the following terms have the following meanings unless indicated otherwise:

"Growth factor receptor inhibitor": an agent that blocks the signal transduction properties of a growth factor receptor. These may act as direct inhibitors of the receptor's tyrosine kinase activity or by inhibiting ligand-stimulated activation of the receptor kinase activity as described in Levitzki and Gazit, 1995 (Science. 267:1782–1788).

"Tyrosine kinase inhibitor": an agent that blocks the tyrosine phosphorylation activity by either being competitive with ATP or via an allosteric interaction with the enzyme as described in Levitzki and Gazit, 1995.

"Protein kinase inhibitor": an agent that blocks protein phosphorylation activity on serine, threonine, or tyrosine residues as described in Levitzki and Gazit, 1995.

"p185 erbB2/HER2/neu receptor inhibitor" or "erbB2 receptor inhibitor": an agent that blocks the signal transduction properties of the erbB2 receptor by either inhibiting the receptor's tyrosine kinase activity or blocking ligand-stimulation of the receptor's kinase activity as described in Levitzki and Gazit, 1995.

"PDGF receptor tyrosine kinase inhibitor": an agent that blocks the signal transduction properties of the platelet-derived growth factor (PDGF) receptor by either inhibiting the receptor's tyrosine kinase activity or blocking PDGF-stimulation of the receptor's kinase activity as described in Kovalenko, M., et.al. (1994). Cancer Res. 54:6106–6114.

"EGF receptor tyrosine kinase inhibitor": an agent that blocks the signal transduction properties of the epidermal growth factor (EGF) receptor by either inhibiting the receptor's tyrosine kinase activity or blocking EGF-stimulation of the receptor's kinase activity as described in Fry et.al (1994), Science 9:1093–1095.

"An antibody directed against the extracellular domain of a growth factor receptor": such antibody blocks the biological activity of the growth factor receptor by inhibiting the binding of ligand and/or preventing ligand-stimulated activation of the receptor tyrosine kinase as described in Mendelsohn, J. (1992) J Nat'l Cancer Inst Monogr 13:125–131.

"A monoclonal antibody which targets the p185 erbB2/HER2/neu receptor" or "A monoclonal antibody which targets the erbB2 receptor": such antibody blocks the biological activity of the HER2 receptor as shown by inhibiting the binding of ligand and/or preventing ligand-stimulated activation of the growth factor receptor kinase as described in Pegram et al., 1998; See also Carter et al. (1992), Proc. Nat'l Acad. Sci. 89:4285–4289.

"A monoclonal antibody which targets the EGF receptor": shown by a monoclonal antibody which inhibits EGF binding and/or EGF-stimulated kinase activity as described in Mendelsohn, J. (1992) J Nat'l Cancer Inst Monogr 13:125–131.

"An antisense molecule directed against a growth factor receptor or other component in the Ras signal pathway": a modified oligonucleotide which interferes with messenger RNA translation (and hence protein expression) of any protein component in the pathway as described in Wang et al., 1998 or Resnicoff, 1998. For a general discussion of antisense technology, see, e.g., *Antisense DNA and RNA*, (Cold Spring Harbor Laboratory, D. Melton, ed., 1988).

"Concurrently": (1) simultaneously in time, or (2) at different times during the course of a common treatment schedule; and "Sequentially": (1) administration of one component of the method ((a) FPT inhibitor, or (b) an additional Ras pathway inhibitor) followed by administration of the other component; after administration of one component, the second component can be administered substantially immediately after the first component, or the second component can be administered after an effective time period after the first component; the effective time period is the amount of time given for realization of maximum benefit from the administration of the first component.

"Downstream" is defined herein as a protein activity (within the Ras signaling pathway) which is regulated by Ras either directly via protein:protein binding or indirectly by a Ras-regulated effector protein. Thus, with reference to FIG. 1, an "element downstream from Ras" can be, e.g., Mek1,2 or Erk1,2.

"Upstream" is defined herein as a protein activity (within the Ras signaling pathay) which would regulate the activity of Ras either directly via protein:protein binding or indirectly by regulating another protein which directly binds to and regulates Ras activity. Thus, an "element upstream of Ras" can be, e.g., erbB2, PDGF receptor, IGF receptor, or EGF receptor.

"Cell death" as described herein is the death of a cell induced either under physiological conditions or by acute injury resulting in the disassembly of the cell organelles and proteins and the abolition of metabolic processes as reviewed in Raff, M. (1998). Nature. 396:119–122. Cell death can be measured, e.g., by the propidium iodide flow cytometry assay described in Dengler et al., (1995) Anticancer Drugs. 6:522–32.

"Apoptosis" as described herein as a form of cell death (programmed cell death) that exhibits stereotypic morphological changes as reviewed in Raff, M. (1998). Nature. 396:119–122. Apoptosis can be measured, e.g., by the propidium iodide flow cytometry assay described in Dengler et al., (1995) Anticancer Drugs. 6:522–32, or by the in situ terminal deoxynucleotidyl transferase and nick translation assay (TUNEL analysis) described in Gorczyca, (1993) Cancer Res 53:1945–51.

"Synergistic" or "synergistic level" is defined herein as an effect achieved by the combination of two components that is greater than the sum of the effects of either of the two components alone (keeping the amount of the component constant). Thus, for example, the phrase "amounts effective to induce a synergistic level of cancer cell death" refers to amounts of two components that achieve a level of cancer cell death (e.g., cell death by apoptosis as measured by the propidium iodide flow cytometry assay described in Dengler et al., (1995) Anticancer Drugs. 6:522–32, or by the in situ terminal deoxynucleotidyl transferase and nick translation assay (TUNEL analysis) described in Gorczyca, (1993) Cancer Res 53:1945–51. ), which is greater than the sum of the effects of either of the two components alone.

"Sustained effect" is defined herein as a prolonged/enhanced apoptotic response to combination treatment with a FPT I and a MEK1,2 inhibitor in comparison to single treatment alone. The consequences of a "sustained effect" can be monitored either by measurement of MAPK activity or cell death or apoptosis, as described in previously. The effective time course for inhibition of MAPK pathway by the individual drugs is dose dependent. However, the experiments herein show that the MEK1,2 inhibitors optimally inhibit the MAPK pathway at or prior to 6 hr of treatment, while SCH 66336 demonstrates optimal MAPK pathway inhibition 12–18 hr after treatment. The MAPK inhibitory effect of SCH 66336 has been shown to last as long as 72 hr after treatment. Thus, combination of the two drugs can result in a "sustained" inhibition of the MAPK pathway for a long period of time, preferably for a period starting at or just prior to 6 hours after treatment, and preferably continuing through to 36 hours, more preferably 72 hours, post treatment. (See, e.g., FIG. 6.

The phrase "killing cancer cells" means induction of cancer cell death of transformed, tumorigenic cancer cells.

More Detailed Illustrations of FPT Inhibitors

Classes of compounds that can be used as the FPT inhibitor include: fused-ringed tricyclic benzocycloheptapyridines, oligopeptides, peptido-mimetic compounds, farnesylated peptido-mimetic compounds, carbonyl piperazinyl compounds, carbonyl piperidinyl compounds, farnesyl derivatives, and natural products and derivatives.

Examples of compounds that are FPT inhibitors and the documents directed to those compounds are given below.

Fused-ring tricyclic benzocycloheptapyridines: WO 95/10514; WO 95/10515; WO 95/10516; WO 96/30363; WO 96/30018; WO 96/30017; WO 96/30362; WO 96/31111; WO 96/31478; WO 96/31477; WO 96/31505; WO 97/23478; International Patent Application No. PCT/US97/17314 (WO 98/15556); International Patent Application No. PCT/US97/15899 (WO 98/11092); International Patent Application No. PCT/US97/15900 (WO 98/11096);

International Patent Application No. PCT/US97/15801 (WO 98/11106); International Patent Application No. PCT/US97/15902 (WO 98/11097); International Patent Application No. PCT/US97/15903 (WO 98/11098); International Patent Application No. PCT/US97/15904; International Patent Application No. PCT/US97/15905 (WO 98/11099); International Patent Application No. PCT/US97/15906 (WO 98/11100); International Patent Application No. PCT/US97/15907 (WO 98/11093); International Patent Application No. PCT/US97/19976 (WO 98/11091); U.S. application Ser. No. 08/877049 now abandoned; U.S. application Ser. No. 08/877366 now U.S. Pat. No. 5,939,416; U.S. application Ser. No. 08/877399 now U.S. Pat. No. 5,852,034; U.S. application Ser. No. 08/877336 now U.S. Pat. No. 5,877,177; U.S. application Ser. No. 08/877269 now abandoned; U.S. application Ser. No. 08/877050 now abandoned; U.S. application Ser. No. 08/877052 now abandoned; U.S. application Ser. No. 08/877051 now abandoned ; U.S. application Ser. No. 08/877498 now abandoned; U.S. application Ser. No. 08/877057 now abandoned; U.S. application Ser. No. 08/877739 now abandoned; U.S. application Ser. No. 08/877677 now U.S. Pat. No. 5,925,639; U.S. application Ser. No. 08/877741 now abandoned; U.S. application Ser. No. 08/877743 now abandoned; U.S. application Ser. No. 08/877457 now abandoned; U.S. application Ser. No. 08/877673 now abandoned; U.S. application Ser. No. 08/876507 now abandoned; and U.S. application Ser. No. 09/216,398.

Some FPT inhibitors are oligopeptides, especially tetrapeptides, or derivatives thereof, based on the formula Cys-$Xaa_1$-$Xaa_2$-$Xaa_3$, where $Xaa_3$ represents a serine, methionine or glutamine residue, and $Xaa_1$ and $Xaa_2$ can represent a wide variety of amino acid residues, but especially those with an aliphatic side-chain. Their derivatives may or may not have three peptide bonds; thus it has been found that reduction of a peptide bond —CO—NH— to a secondary amine grouping, or even replacement of the nitrogen atoms in the peptide chain with carbon atoms (provided that certain factors such as general shape of the molecule and separation of the ends are largely conserved) affords compounds that are frequently more stable than the oligopeptides and, if active, have longer activity. Such compounds are referred to herein as peptido-mimetic compounds.

Oligopeptides (mostly tetrapeptides but also pentapeptides) including the formula Cys-$Xaa_1$-$Xaa_2$-$Xaa_3$: EPA 461,489; EPA 520,823; EPA 528,486; and WO 95/11917.

Peptido-mimetic compounds—especially Cys-Xaa-Xaa-Xaa-mimetics: EPA 535,730; EPA 535,731; EPA 618,221; WO 94/09766; WO 94/10138; WO 94/07966; U.S. Pat Nos. 5,326,773; 5,340,828; 5,420,245; WO 95/20396; U.S. Pat. No. 5,439,918; and WO 95/20396.

Farnesylated peptido-mimetic compounds—specifically farnesylated Cys-Xaa-Xaa-Xaa-mimetic: GB-A 2,276,618.

Other peptido-mimetic compounds: U.S. Pat. No. 5,352,705; WO 94/00419; WO 95/00497; WO 95/09000; WO 95/09001; WO 95/12612; WO 95/25086; EPA 675,112; and FR-A 2,718,149.

Farnesyl derivatives: EPA 534,546; WO 94/19357; WO 95/08546; EPA 537,007; and WO 95/13059.

Natural products and derivatives: WO 94/18157; U.S. Pat. No. 5,430,055; GB-A 2,261,373; GB-A 2,261,374; GB-A 2,261,375; U.S. Pat. Nos. 5,420,334; 5,436,263.

Other compounds: WO 94/26723; WO 95/08542; U.S. Pat. No. 5,420,157; WO 95/21815; WO 96/31501; WO 97/16443; WO 97/21701; U.S. Pat. Nos. 5,578,629; 5,627,202; WO 96/39137; WO 97/18813; WO 97/27752WO 97/27852; WO 97/27853; WO 97/27854; WO 97/36587; WO 97/36901; WO 97/36900; WO 97/36898; WO 97/36897; WO 97/36896; WO 97/36892; WO 97/36891; WO 97/36890; WO 97/36889; WO 97/36888; WO 97/36886; WO 97/36881; WO 97/36879; WO 97/36877; WO 97/36876; WO 97/36875; WO 97/36605; WO 97/36593; WO 97/36592; WO 97/36591; WO 97/36585; WO 97/36584; and WO 97/36583.

A plasmid encoding an α- and a β-unit of an FPT, and describing an assay therefor: WO 94/10184.

Reference is also made to U.S. application Ser. No. 09/217,335 now U.S. Pat. No. 6,096,757 and International Patent application No. PCT/ US98/26224, which disclose a variety of methods for combining FPT inhibitors with chemotherapeutic agents and/or radiation therapy in the treatment of proliferative disease such as cancer.

All of the foregoing documents directed to compounds that are FPT inhibitors are incorporated herein by reference thereto.

A review of many such compounds is given by Graham in *Exp. Opin. Ther. Patents* (1995) 5(12): 1269–1285.

It will be understood that the breadth of a chemical formula in a patent specification may not enable one to classify all compounds therein under one of the headings above. For example, the monoterpenyl chain in the farnesyl derivatives may be extended, e.g. by a number of methylene groups or even another isoprene residue.

The tetrapeptides of the formula Cys-$Xaa_1$-$Xaa_2$-$Xaa_3$ have an amino-terminal cysteine residue. A tetrapeptide of that type forms the carboxyl-terminal of ras. Such tetrapeptides are capable of binding with FPT and competing with ras. Compounds of similar structure but having at least one of the carbonyl groups of the tetrapeptide replaced by a hydrocarbyl group such as a methylene group and classified above as peptido-mimetic compounds are also capable of binding with FPT and competing with ras, but are generally more resistant to enzymatic degradation in vivo.

FPT INHIBITORS—EXEMPLIFIED COMPOUNDS

The following documents disclose preferred FPT inhibitors for use in the present invention. The documents also disclose methods of inhibiting abnormal cell growth (e.g., tumors) using the compounds disclosed in the document. The radicals and formulae designations defined herein for a particular document apply only to the compounds described in that document.

WO 95/10516 published Apr. 20, 1995 and WO 96/30363 published Oct. 3, 1996 disclose compounds of formula 1.0:

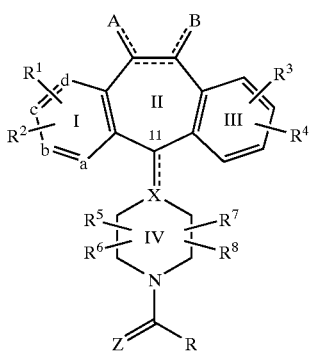

(1.0)

or a pharmaceutically acceptable salt or solvate thereof, wherein:
one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or
each of a, b, c, and d is independently selected from $CR^1$ and $CR^2$;
each $R^1$ and each $R^2$ is independently selected from H, halo, —$CF_3$, —$OR^{10}$, —$COR^{10}$, —$SR^{10}$, —$S(O)_tR^{11}$ (wherein t is 0, 1 or 2), —SCN, —$N(R^{10})_2$, —$NO_2$, —$OC(O)R^{10}$, —$CO_2R^{10}$, —$OCO_2R^{11}$, —CN, —NHC(O)$R^{10}$, —$NHSO_2R^{10}$, —$CONHR^{10}$, —$CONHCH_2CH_2OH$, —$NR^{10}COOR^{11}$, —$SR^{11}C(O)OR^{11}$,

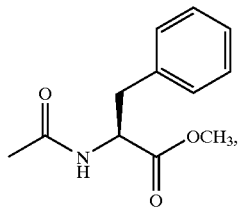

—$SR^{11}N(R^{75})_2$ (wherein each $R^{75}$ is independently selected from H and —$C(O)OR^{11}$), benzotriazol-1-yloxy, tetrazol-5-ylthio, substituted tetrazol-5-ylthio, alkynyl, alkenyl and alkyl, said alkyl or alkenyl group optionally being substituted with halo, —$OR^{10}$ or —$CO_2R^{10}$;
$R^3$ and $R^4$ are the same or different and each independently represents H or any of the substituents of $R^1$ and $R^2$, or $R^3$ and $R^4$ taken together represent a saturated or unsaturated $C_5$–$C_7$ ring fused to the benzene ring;
each of $R^5$, $R^6$, $R^7$ and $R^8$ independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, or $OPO_3R^{10}$, or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;
$R^{10}$ represents H, alkyl, aryl, or aralkyl;
$R^{11}$ represents alkyl or aryl;
X represents N, CH or C, which C may contain an optional double bond, represented by the dotted line, to carbon atom 11;

the dotted line between carbon atoms 5 and 6 represents an optional double bond, such that when a double bond is present, A, and B independently represent —$R^{10}$, halo, —$OR^{11}$, —$OCO_2R^{11}$ or —$OC(O)R^{10}$, and when no double bond is present between carbon atoms 5 and 6, each of A and B independently represents $H_2$, —$(OR^{11})_2$, (H and halo), dihalo, (alkyl and H), (alkyl)$_2$, (H and —$OC(O)R^{10}$), (H and —$OR^{10}$), =O, (aryl and H), =$NOR^{10}$, or —O—$(CH_2)_p$—O— wherein p is 2, 3 or 4;
R represents $R^{40}$, $R^{42}$, $R^{44}$, or $R^{54}$, as defined below;
$R^{40}$ represents H, aryl, alkyl, cycloalkyl, alkenyl, alkynyl or —D wherein —D represents

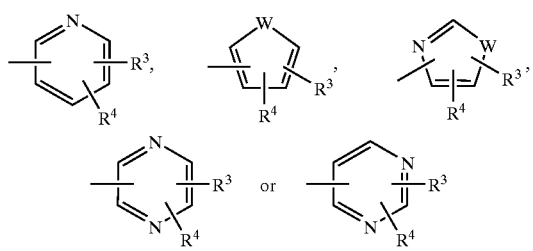

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1–3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein —D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or
$R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, and —$NHSO_2CF_3$, which group is preferably located in the para position of the phenyl ring; or
$R^{40}$ represents a group selected from

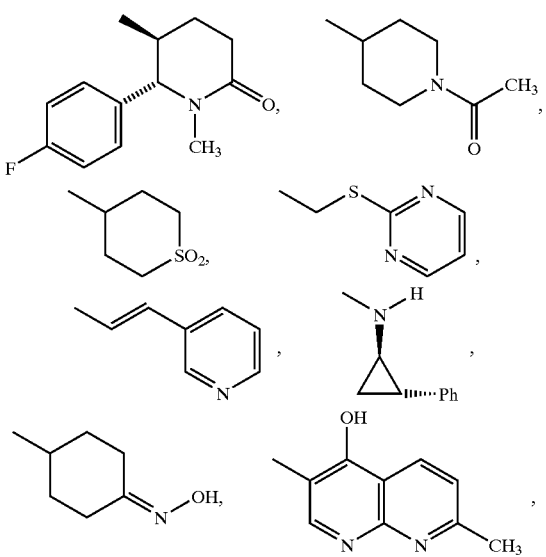

-continued

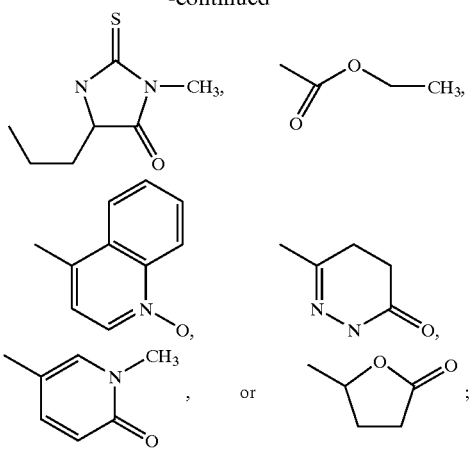

$R^{42}$ represents

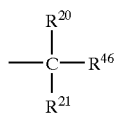

wherein $R^{20}$, $R^{21}$ and $R^{46}$ are each independently selected from the group consisting of:
(1) H;
(2) —$(CH_2)_q SC(O)CH_3$ wherein q is 1 to 3;
(3) —$(CH_2)_q OSO_2 CH_3$ wherein q is 1 to 3;
(4) —OH;
(5) —CS—$(CH_2)_w$-(substituted phenyl) wherein w is 1 to 3 and the substitutents on said substituted phenyl group are the same substitutents as described under (12) below for substituted phenyl;
(6) —$NH_2$;
(7) —NHCBZ;
(8) —$NHC(O)OR^{22}$ wherein $R^{22}$ is an alkyl group having from 1 to 5 carbon atoms, or $R^{22}$ represents phenyl substituted with 1 to 3 alkyl groups;
(9) alkyl;
(10) —$(CH_2)_k$-phenyl wherein k is 1 to 6;
(11) phenyl;
(12) substituted phenyl wherein the substituents are selected from the group consisting of: halo, $NO_2$, —OH, —$OCH_3$, —$NH_2$, —$NHR^{22}$, —$N(R^{22})_2$, alkyl, —$O(CH_2)_t$-phenyl (wherein t is from 1 to 3), and —$O(CH_2)_t$-substituted phenyl (wherein t is from 1 to 3);
(13) naphthyl;
(14) substituted naphthyl, wherein the substituents are as defined for substituted phenyl under (12) above;
(15) bridged polycyclic hydrocarbons having from 5 to 10 carbon atoms;
(16) cycloalkyl having from 5 to 7 carbon atoms;
(17) heteroaryl;
(18) hydroxyalkyl;
(19) substituted pyridyl or substituted pyridyl N-oxide wherein the substituents are selected from methylpyridyl, morpholinyl, imidazolyl, 1-piperidinyl, 1-(4-methylpiperazinyl), —$S(O)_x R^{11}$, and any of the substituents given under (12) above for substituted phenyl, and said substitutents are bound to a ring carbon by replacement of the hydrogen bound to said carbon;

(20)

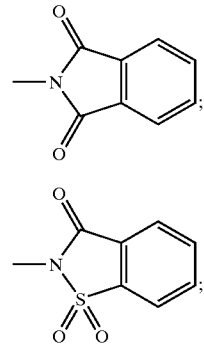

(21)

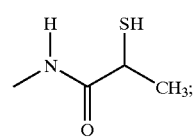

(22)

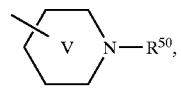

(23) —$NHC(O)$—$(CH_2)_k$-phenyl or —$NH(O)$—$(CH_2)_k$-(substituted phenyl), wherein said k is as defined under (10) above;
(24) piperidine Ring V:

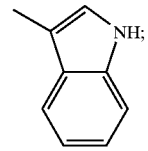

wherein $R^{50}$ represents H, alkyl, alkylcarbonyl, alkoxycarbonyl, haloalkyl, or —$C(O)NH(R^{10})$ wherein $R^{10}$ is H or alkyl;
(25) —$NHC(O)CH_2 C_6 H_5$ or —$NHC(O)CH_2$-(substituted $C_6 H_5$);
(26) —$NHC(O)OC_6 H_5$;

(27)

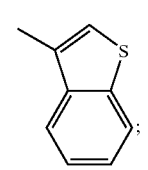

(28)

(29)

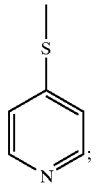

(30) —OC(O)-heteroaryl (for example pyridine-4-carbonyloxy)
(31) —O-alkyl (e.g., —$OCH_3$);

(32) —CF$_3$;

(33) —CN;

(34) a heterocycloalkyl group of the formula

(35) a piperidinyl group of the formula

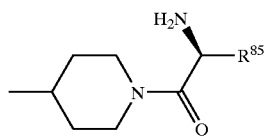

wherein R$^{85}$ is H, alkyl, or alkyl substituted by —OH or —SCH$_3$; or

R$_{20}$ and R$^{21}$ taken together form an =O group and the remaining R$^{46}$ is as defined above; or two of R$^{20}$, R$^{21}$ and R$^{46}$ taken together form piperidine Ring V

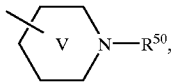

wherein R$^{50}$ is as defined under (24) above;

with the proviso that R$^{46}$, R$^{20}$ and R$^{21}$ are selected such that the carbon atom to which they are bound is not bonded to more than one heteroatom;

R$^{44}$ represents —NR$^{25}$R$^{48}$ wherein R$^{25}$ represents heteroaryl, N-methylpiperidinyl or aryl, and R$^{48}$ represents H or alkyl;

R$^{54}$ represents an N-oxide heterocyclic group of the formula (i), (ii), (iii) or (iv):

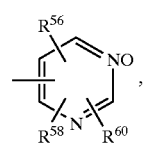

(i)

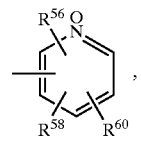

(ii)

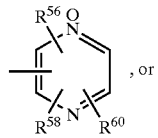

(iii)

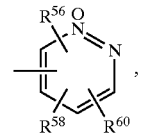

(iv)

wherein R$^{56}$, R$^{58}$, and R$^{60}$ are the same or different and each is independently selected from H, halo, —CF$_3$, —OR$^{10}$, —C(O)R$^{10}$, —SR$^{10}$, —S(O)$_e$R$^{11}$ (wherein e is 1 or 2), —N(R$^{10}$)$_2$, —NO$_2$, —CO$_2$R$^{10}$, —OCO$_2$R$^{11}$, —OCOR$^{10}$, alkyl, aryl, alkenyl and alkynyl, which alkyl may be substituted with —OR$^{10}$, 13 SR$^{10}$ or —N(R$^{10}$)$_2$ and which alkenyl may be substituted with OR$^{11}$ or SR$^{11}$; or R$^{54}$ represents an N-oxide heterocyclic group of the formula (ia), (iia), (iiia) or (iva):

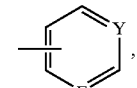

(ia)

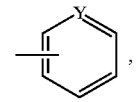

(iia)

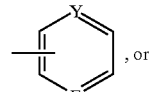

(iiia)

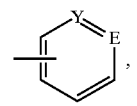

(iva)

wherein Y represents N$^+$—O$^-$ and E represents N; or

R$^{54}$ represents an alkyl group substituted with one of said N-oxide heterocyclic groups (i), (ii), (iii), (iv), (ia), (iia), (iiia) or (iva); and Z represents O or S such that R can be taken in combination with R$^5$, R$^6$, R$^7$ or R$^8$ as defined above, or R represents R$^{40}$, R$^{42}$, R$^{44}$ or R$^{54}$.

WO 97/23478 published Jul. 3, 1997, and expressly incorporated herein by reference, discloses the compounds:

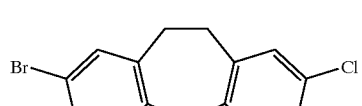

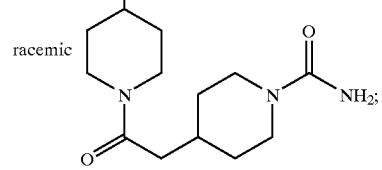

(1.0)

racemic

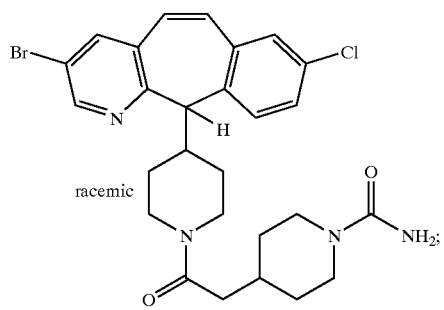
(2.0)
racemic
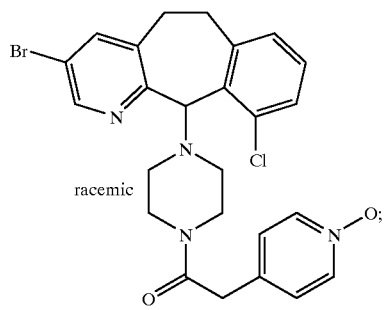
(3.0)
racemic
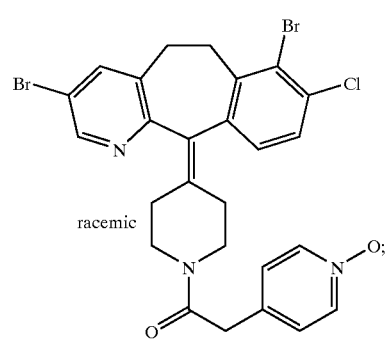
(5.0)
racemic
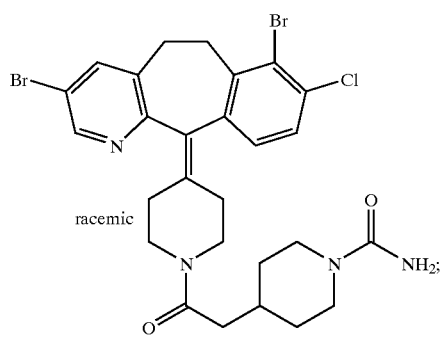
(6.0)
racemic
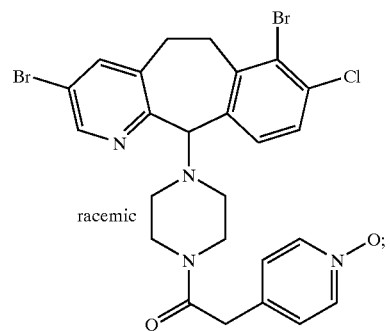
(7.0)
racemic
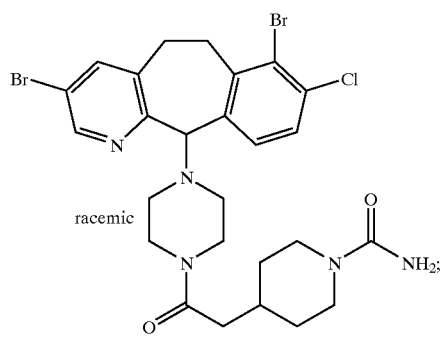
(7.0A)
racemic
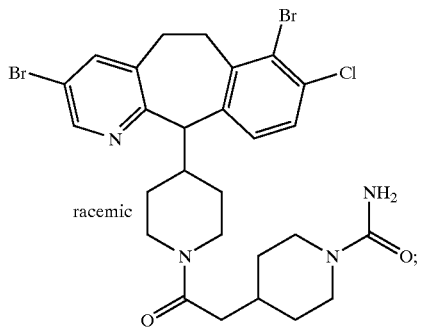
(8.0)
racemic
(8.0A)
racemic
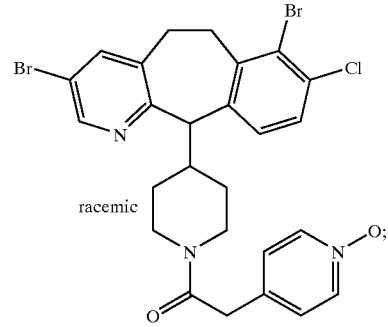
(9.0)
racemic
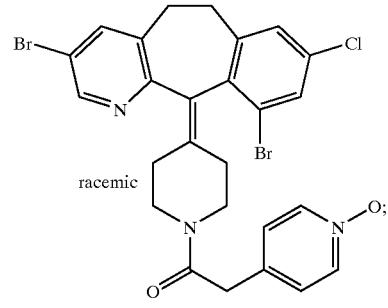
(10.0)
racemic

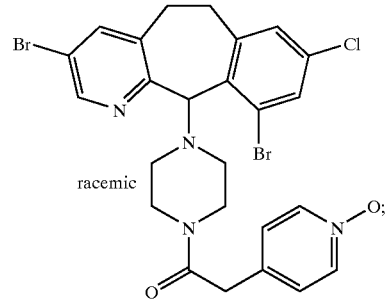
(11.0)
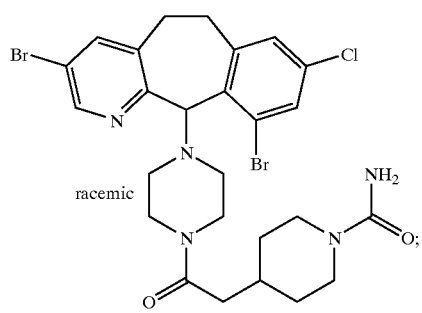
(12.0)
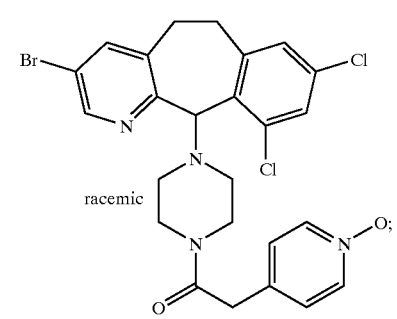
(13.0)
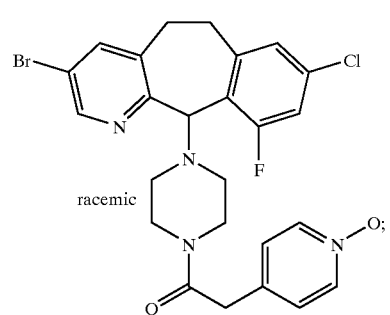
(14.0)
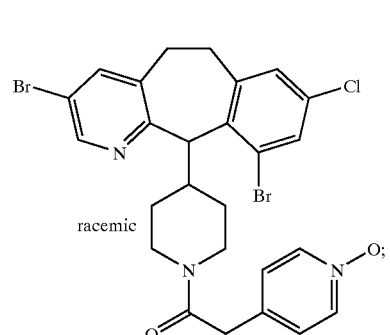
(15.0)
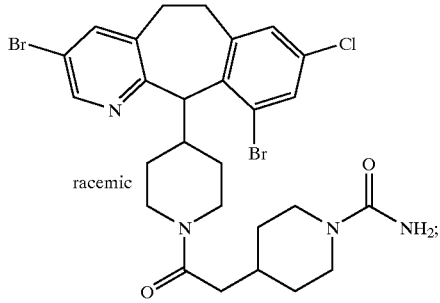
(16.0)
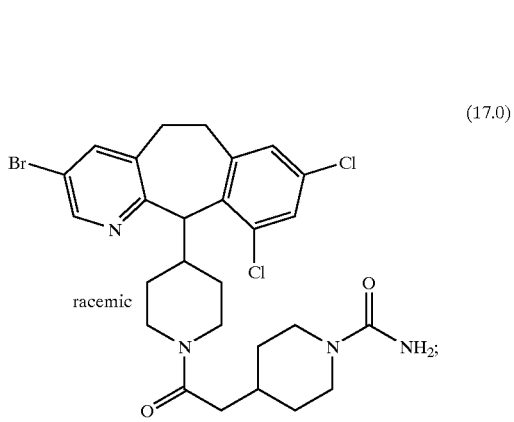
(17.0)
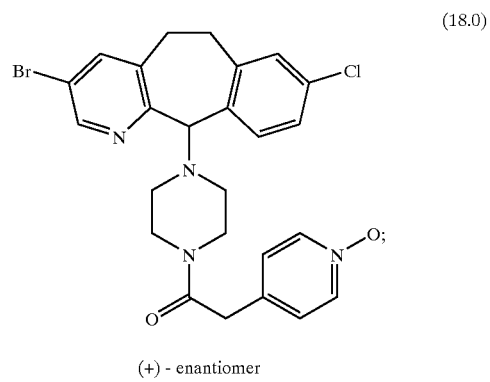
(18.0)
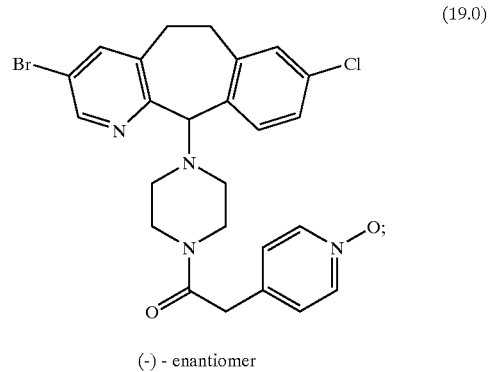
(19.0)

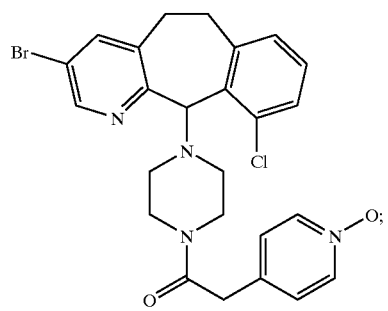
(20.0)
(+) - enantiomer
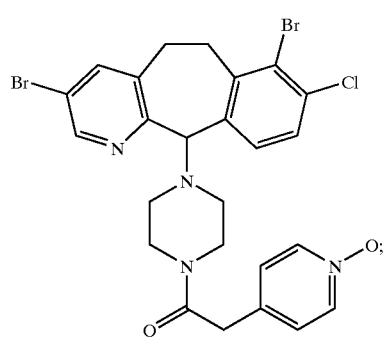
(21.0)
(+) - enantiomer
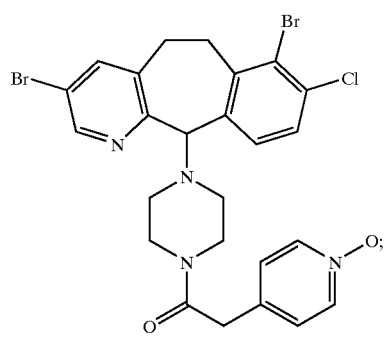
(22.0)
(-) - enantiomer
(23.0)
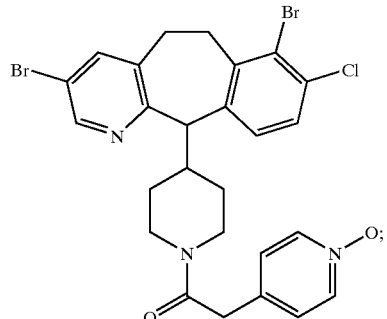
(24.0)
(+) - enantiomer
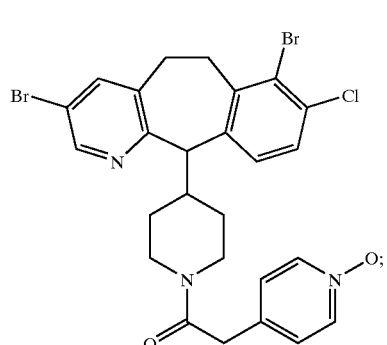
(25.0)
(-) - enantiomer
(26.0)
(+) - enantiomer
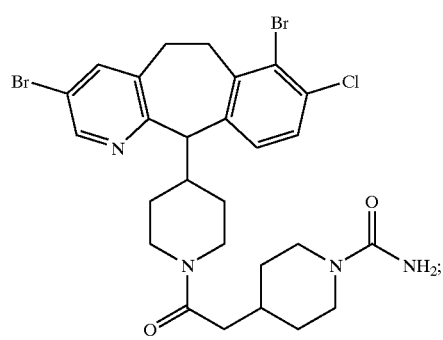
(27.0)
(-) - enantiomer (28.0) (−)-enantiomer (29.0) (+)-enantiomer (30.0) (−)-enantiomer (31.0) (+)-enantiomer (32.0) (+)-enantiomer (33.0) (−)-enantiomer (34.0) (+)-enantiomer (35.0) (−)-enantiomer -continued
(36.0)
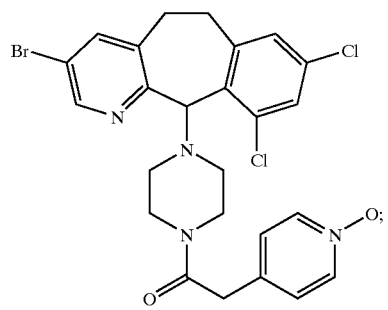
(+) - enantiomer
(37.0)
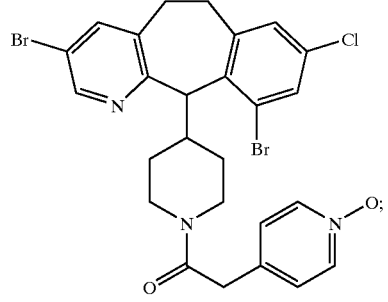
(+) - enantiomer
(38.0)
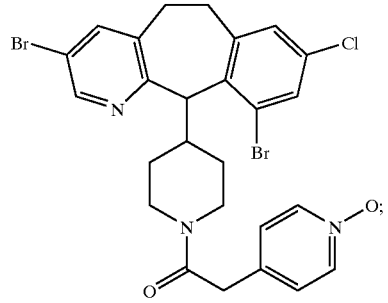
(-) - enantiomer
(39.0)
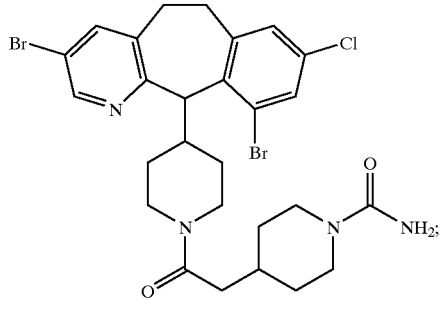
(+) - enantiomer
-continued
(40.0)
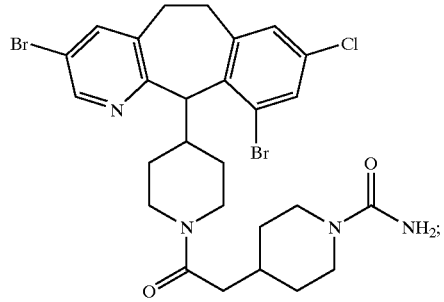
(-) - enantiomer
(41.0)
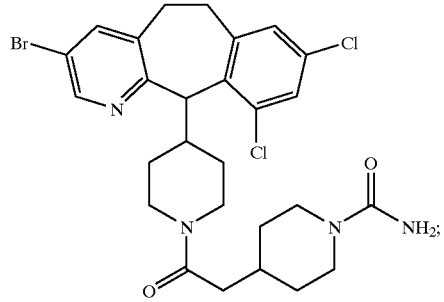
(+) - enantiomer
(42.0)
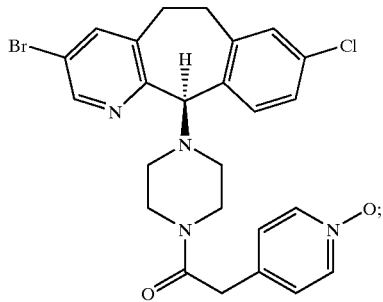
(43.0)
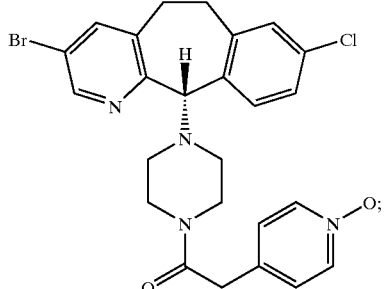
(44.0)
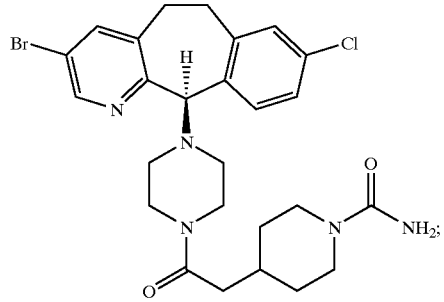

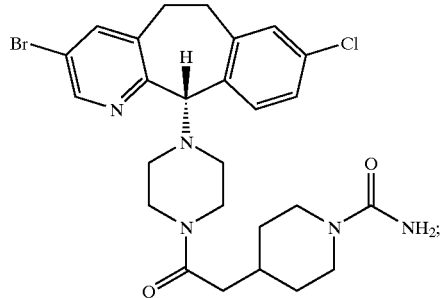
(45.0)
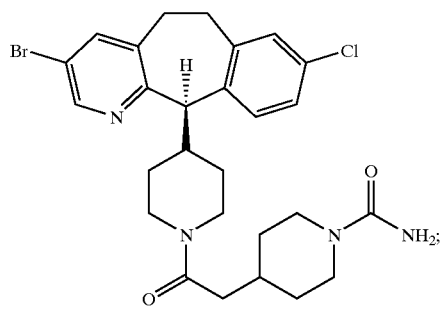
(46.0)
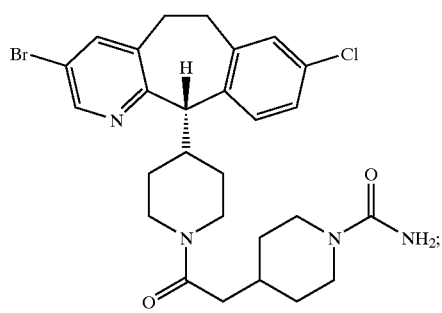
(47.0)
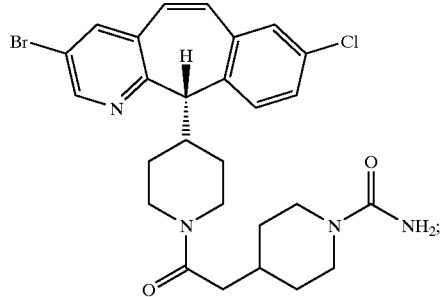
(48.0)
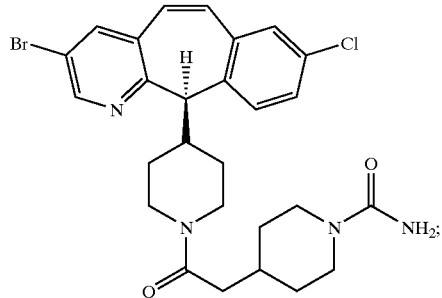
(49.0)
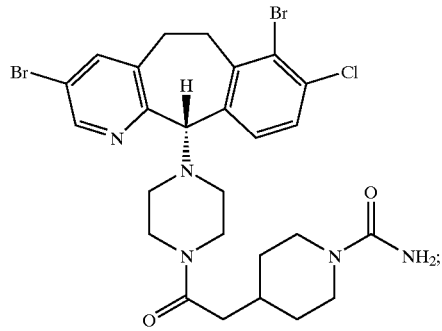
(50.0)
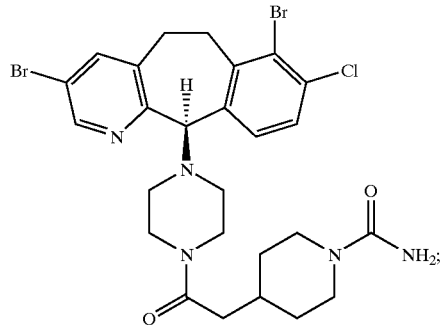
(51.0)
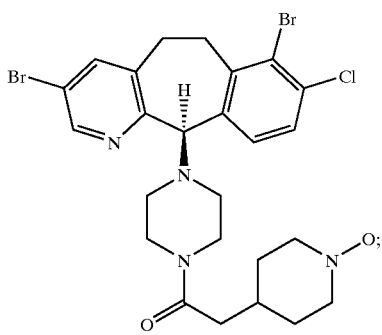
(52.0)
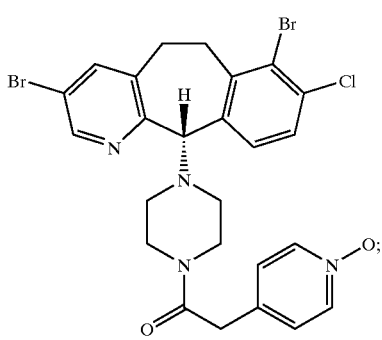
(53.0)

(54.0)
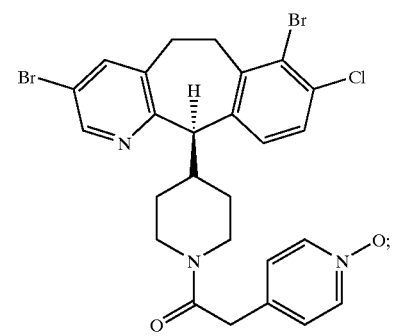
(55.0)
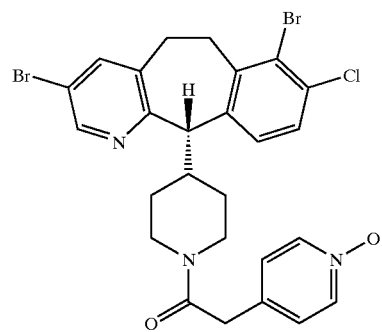
(56.0)
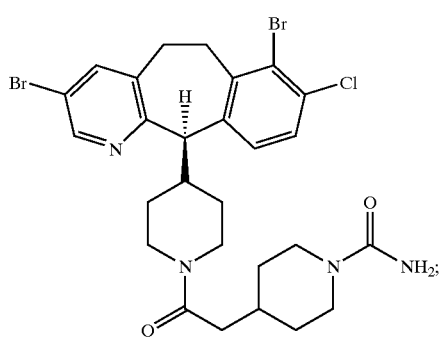
(57.0)
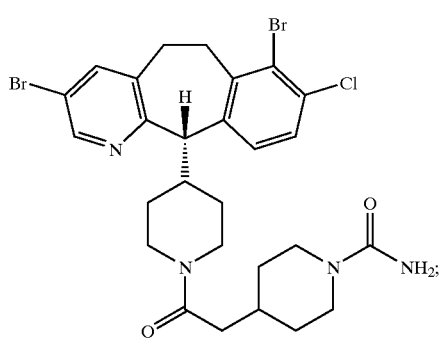
(58.0)
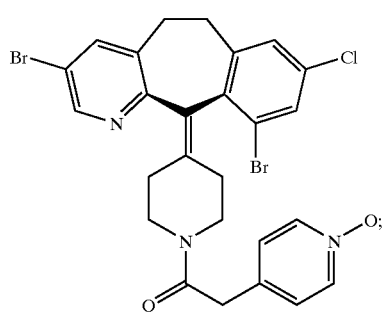
(59.0)
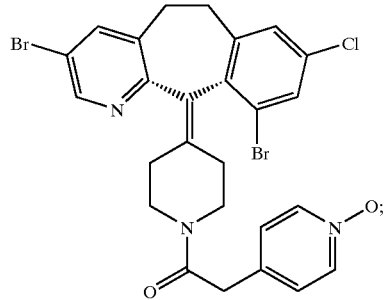
(60.0)
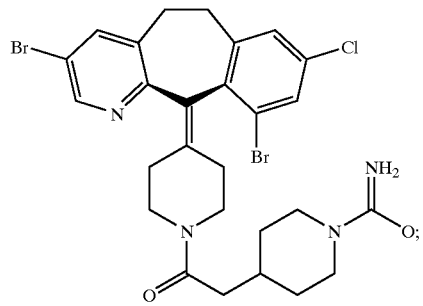
(61.0)
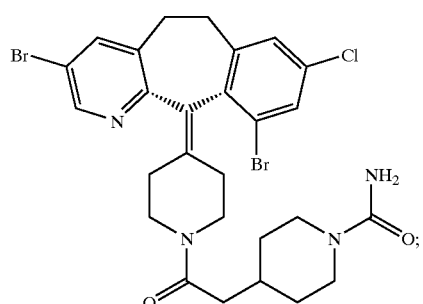
(62.0)
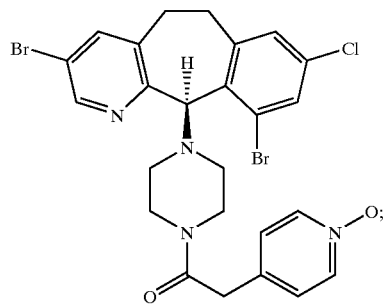
(63.0)
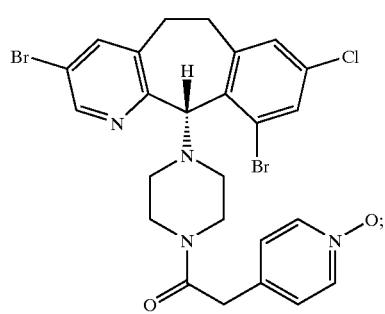

-continued
(64.0)
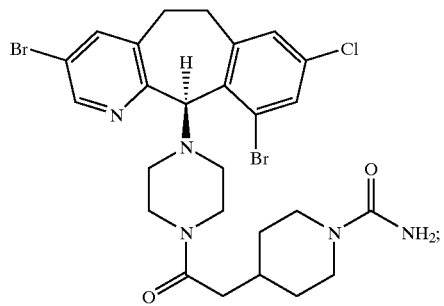
(65.0)
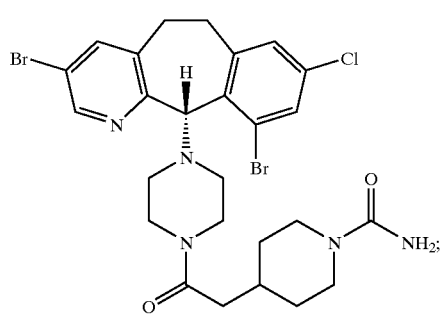
(66.0)
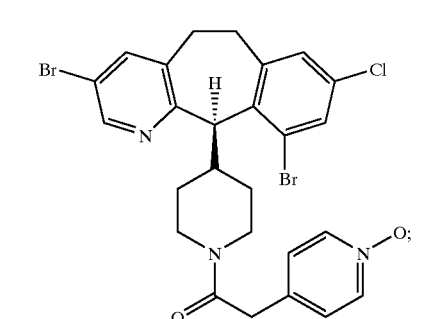
(67.0)
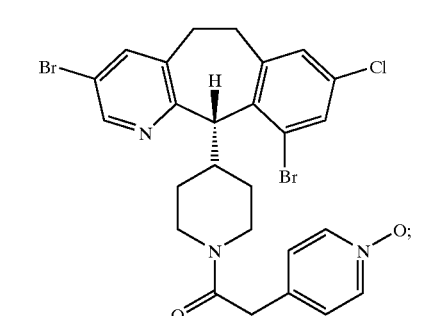
(68.0)
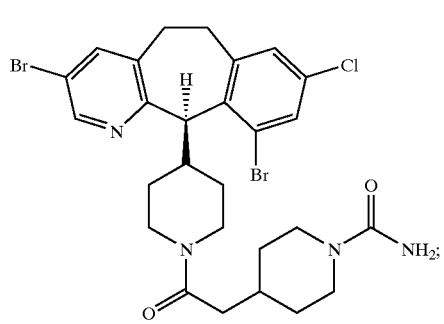
-continued
(69.0)
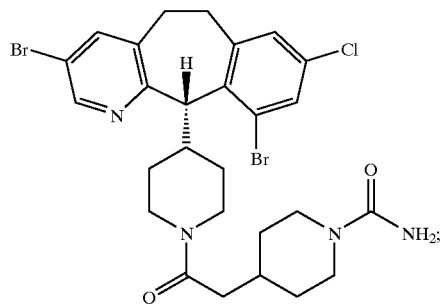
(70.0)
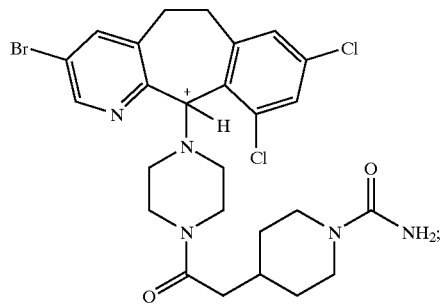
(71.0)
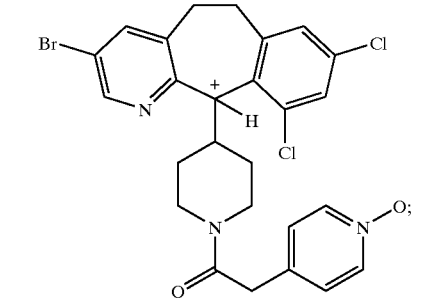
(72.0)
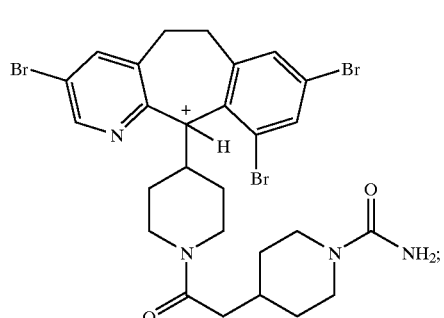
(73.0)
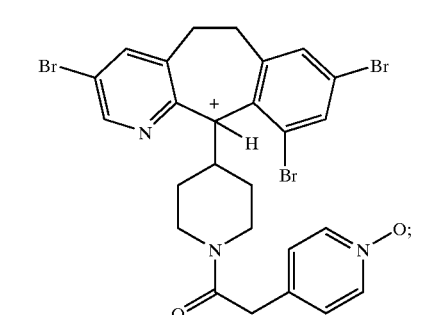

-continued

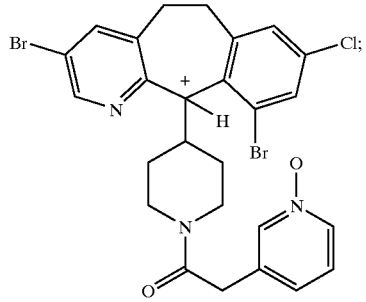
(74.0)

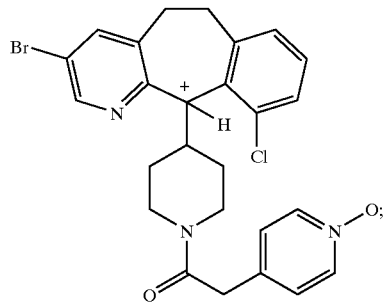
(75.0)

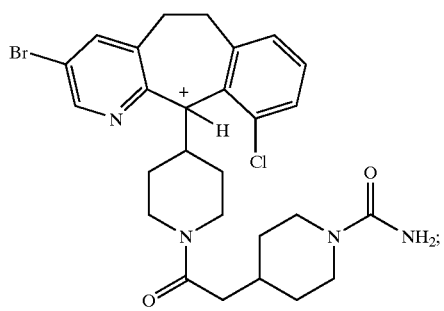
(76.0)

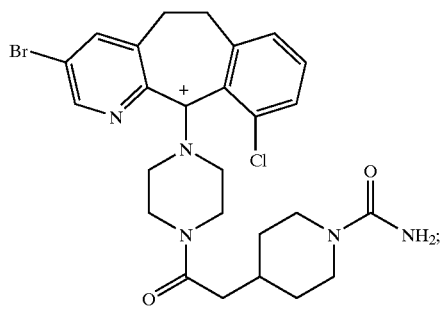
(77.0)

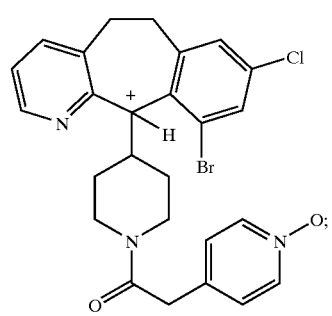
(78.0)

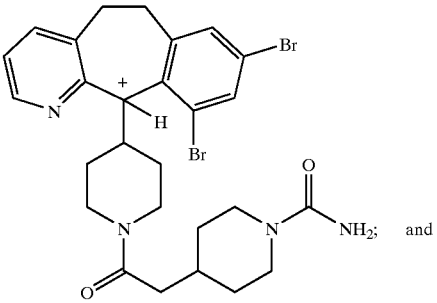
(79.0)

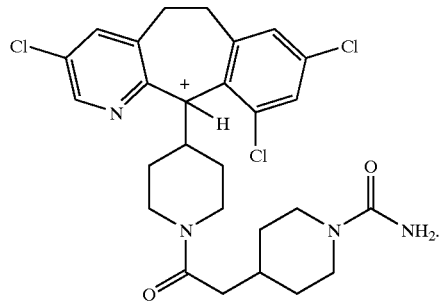
and

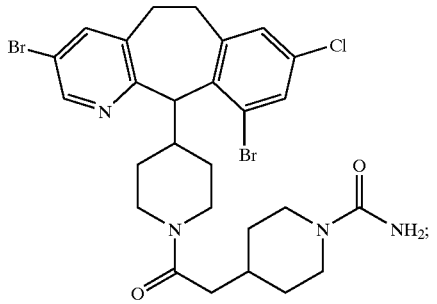
(80.0)

or pharmaceutically acceptable salts thereof.

A preferred compound for use as an FPT inhibitor in the method of the present invention has the formula:

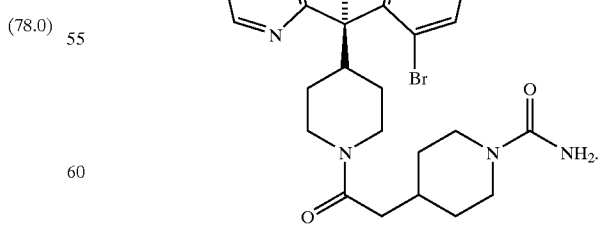

i.e., the compound 4-[2-[4-[(8-chloro-3,10-dibromo-6,11-dihydro-5H-benzo[5,6]cyclohepta[1,2-b]pyridin-11-yl)-1-piperidinyl]-2-oxoethyl]-1-piperidinecarboxamide, preferably the (+)-isomer thereof, which has the structure See also U.S. Pat. No. 5,719,148 (issued Feb. 17, 1998) and U.S. Pat. No. 5,874,442 (issued Feb. 23, 1999), which are each expressly incorporated herein by reference.

U.S. patent application U.S. Ser. No. 09/216,398, now abandoned, expressly incorporated herein by reference, discloses compounds useful for the inhibition of FPT represented by the formula:

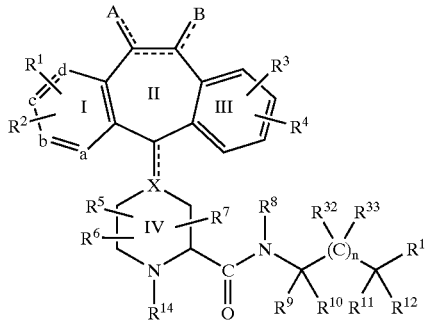

(1.0)

or a pharmaceutically acceptable salt or solvate thererof, wherein:
one of a, b, c and d represents N or N⁺O⁻, and the remaining a, b, c and d groups represent $CR^1$ or $CR^2$; or
each of a, b, c, and d are independently selected from $CR^1$ or $CR^2$;
X represents N or CH when the optional bond (represented by the dotted line) is absent, and represents C when the optional bond is present;
the dotted line between carbon atoms 5 and 6 represents an optional bond, such that when a double bond is present, A and B independently represent —$R^{15}$, halo, —$OR^{16}$, —$OCO_2R^{16}$ or —$OC(O)R^{15}$, and when no double bond is present between carbon atoms 5 and 6, A and B each independently represent $H_2$, —$(OR^{16})_2$, H and halo, dihalo, alkyl and H, (alkyl)$_2$, —H and —$OC(O)R^{15}$, H and —$OR^{15}$, =O, aryl and H, =$NOR^{15}$ or —O—$(CH_2)_p$—O—wherein p is 2, 3 or 4;
each $R^1$ and each $R^2$ is independently selected from H, halo, —$CF_3$, —$OR^{15}$ (e.g., —$OCH_3$), —$COR^{15}$, —$SR^{15}$ (e.g., —$SCH_3$ and —$SCH_2C_6H_5$), —$S(O)_tR^{16}$ (wherein t is 0, 1 or 2, e.g., —$SOCH_3$ and —$SO_2CH_3$), —$N(R^{15})_2$, —$NO_2$, —$OC(O)R^{15}$, —$CO_2R^{15}$, —$OCO_2R^{16}$, —CN, —$NR^{15}COOR^{16}$, —$SR^{16}C(O)$ $OR^{16}$ (e.g., —$SCH_2CO_2CH_3$), —$SR^{16}N(R^{17})_2$ wherein each $R^{17}$ is independently selected from H and —C(O) $OR^{16}$ provided that $R^{16}$ is not —$CH_2$— (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{15}$ or —$C_2R^{15}$;
$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);
$R^5$, $R^6$, and $R^7$ each independently represents H, —$CF_3$, —$COR^{15}$, alkyl or aryl, said alkyl or aryl optionally being substituted with —$OR^{15}$, —$SR^{15}$—$S(O)_tR^{16}$, —$NR^{15}COOR^{16}$, —$N(R^{15})_2$, —$NO_2$, —$COR^{15}$, —$OCOR^{15}$, —$OCO_2R^{16}$, —$CO_2R^{15}$, $OPO_3R^{15}$, or $R^5$ is combined with $R^6$ to represent =O or =S;
$R^8$ is selected from: H, $C_3$ to $C_4$ alkyl (preferably branched chain alkyl, and most preferably $C_4$ to $C_7$ branched chain alkyl), aryl, arylalkyl, heteroaryl, heteroarylalkyl, cycloalkyl, cycloalkylalkyl, substituted alkyl, substituted aryl, substituted arylalkyl, substituted heteroaryl, substituted heteroarylalkyl, substituted cycloalkyl, substituted cycloalkylalkyl;
the substutuents for the $R^8$ substituted groups being selected from: alkyl, aryl, arylalkyl, cycloalkyl, —$N(R^{18})_2$, —$OR^{18}$, cycloalkyalkyl, halo, CN, —C(O) $N(R^{18})_2$, —$SO_2N(R^{18})_2$ or —$CO_2R^{18}$; provided that the —$OR^{18}$ and —$N(R^{18})_2$ substituents are not bound to the carbon that is bound to the N of the —C(O) $NR^8$— moiety;
each $R^{18}$ is independently selected from: H, alkyl, aryl, arylalkyl, heteroaryl or cycloalkyl;
$R^9$ and $R^{10}$ are independently selected from: H, alkyl, aryl, arylalkyl, heteroaryl, heteroarylalkyl, cycloalkyl or —$CON(R^{18})_2$ (wherein $R^{18}$ is as defined above); and the substitutable $R^9$ and $R^{10}$ groups are optionally substituted with one or more (e.g., 1–3) substituents selected from: alkyl (e.g., methyl, ethyl, isopropyl, and the like), cycloalkyl, arylalkyl, or heterarylalkyl (i.e., the $R^9$ and/or $R^{10}$ groups can be unsubtituted or can be substituted with 1–3 of the substitutents described above, except when $R^9$ and/or $R^{10}$ is H); or
$R^9$ and $R^{10}$ together with the carbon atom to which they are bound, form a $C_3$ to $C_6$ cycloalkyl ring;
$R^{11}$ and $R^{12}$ are independently selected from: H, alkyl, aryl, arylalkyl, heteroaryl, heteroarylalkyl, cycloalkyl, —$CON(R^{18})_2$—$OR^{18}$ or —$N(R^{18})_2$; wherein $R^{18}$ is as defined above; provided that the —$OR^{18}$ and —$N(R^{18})_2$ groups are not bound to a carbon atom that is adjacent to a nitrogen atom; and wherein said substitutable $R^{11}$ and $R^{12}$ groups are optionally substituted with one or more (e.g., 1–3) substituents selected from: alkyl (e.g., methyl, ethyl, isopropyl, and the like), cycloalkyl, arylalkyl, or heterarylalkyl; or
$R^{11}$ and $R^{12}$ together with the carbon atom to which they are bound, form a $C_3$ to $C_6$ cycloalkyl ring;
$R^{13}$ is an imidazolyl ring selected from:

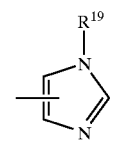

(2.0)

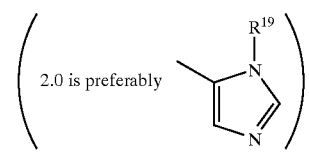

2.0 is preferably (2.1)

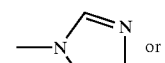

or (4.0)

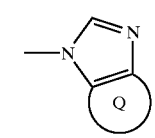

(4.1)

wherein $R^{19}$ is selected from: (1) H, (2) alkyl, (3) alkyl, (4) aryl, (5) arylalkyl, (6) substituted arylalkyl wherein the substituents are selected from halo (e.g., F and Cl) or CN, (7) —C(aryl)$_3$ (e.g., —C(phenyl)$_3$, i.e., trityl) or (8) cycloalkyl;

said imidazolyl ring 2.0 or 2.1 optionally being substituted with one or two substituents and said imidazole ring 4.0 optionally being substituted with 1–3 substituents and said imidazole ring 4.1 being optionally substituted with one substituent wherein said optional substituents for rings 2.0, 2.1, 4.0 and 4.1 are bound to the carbon atoms of said imidazole rings and are independently selected from: —NHC(O)$R^{18}$, —C($R^{34}$)$_2$O$R^{35}$, —O$R^{18}$, —S$R^{18}$, F, Cl, Br, alkyl, aryl, arylalkyl, cycloalkyl, or —N($R^{18}$)$_2$; $R^{18}$ is as defined above; each $R^{34}$ is independently selected from H or alkyl (preferably —CH$_3$), preferably H; $R^{35}$ is selected from H, —C(O)O$R^{20}$, or —C(O)NH$R^{20}$, and $R^{20}$ is as defined below (preferably $R^{20}$ is alkyl or cycloalkyl, most preferably cyclopentyl or cyclohexyl); Q represents an aryl ring (e.g., phenyl), a cycloalkyl ring (e.g., cyclopentyl or cyclohexyl) or a heteroaryl ring (e.g., furanyl, pyrrolyl, thienyl, oxazolyl or thiazolyl); (examples of the —C($R^{34}$)$_2$O$R^{35}$ group include —CH$_2$OH, —CH$_2$OC(O)O$R^{20}$ and —CH$_2$OC(O)NH$R^{20}$);

$R^{14}$ is selected from:

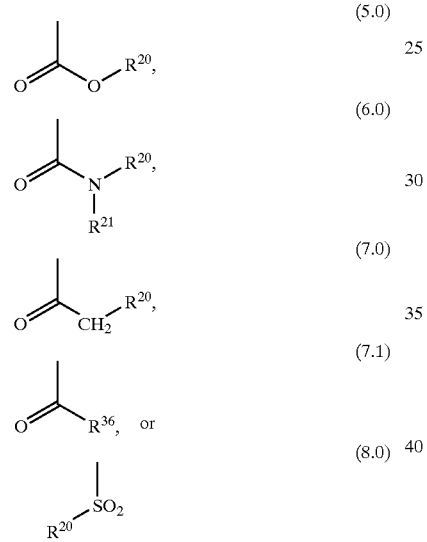

$R^{15}$ is selected from: H, alkyl, aryl or arylalkyl;

$R^{16}$ is selected from: alkyl or aryl;

$R^{20}$ is selected from: H, alkyl, alkoxy, aryl, arylalkyl, cycloalkyl, heteroaryl, heteroarylalkyl or heterocycloalkyl, provided that $R^{20}$ is not H when $R^{14}$ is group 5.0 or 8.0;

when $R^{20}$ is other than H, then said $R^{20}$ group is optionally substituted with one or more (e.g., 1–3) substituents selected from: halo, alkyl, aryl, —O$R^{18}$ or —N($R^{18}$)$_2$, wherein each $R^{18}$ group is the same or different, and wherein $R^{18}$ is as defined above, provided that said optional substituent is not bound to a carbon atom that is adjacent to an oxygen or nitrogen atom;

$R^{21}$ is selected from: H, alkyl, aryl, arylalkyl, cycloalkyl, heteroaryl, heteroarylalkyl or heterocycloalkyl;

when $R^{21}$ is other than H, then said $R^{21}$ group is optionally substituted with one or more (e.g., 1–3) substituents selected from: halo, alkyl, aryl, —O$R^{18}$ or —N($R^{18}$)$_2$, wherein each $R^{18}$ group is the same or different, and wherein $R^{18}$ is as defined above, provided that said optional substituent is not bound to a carbon atom that is adjacent to an oxygen or nitrogen atom;

n is 0–5;

each $R^{32}$ and $R^{33}$ for each n (i.e., for each —C($R^{32}$)($R^{33}$)— group), are independently selected from: H, alkyl, aryl, arylalkyl, heteroaryl, heteroarylalkyl, cycloalkyl, —CON($R^{18}$)$_2$, —O$R^{18}$ or —N($R^{18}$)$_2$; wherein $R^{18}$ is as defined above; and wherein said substitutable $R^{32}$ and $R^{33}$ groups are optionally substituted with one or more (e.g., 1–3) substituents selected from: alkyl (e.g., methyl, ethyl, isopropyl, and the like), cycloalkyl, arylalkyl, or hetarylalkyl; or $R^{32}$ and $R^{33}$ together with the carbon atom to which they are bound, form a $C_3$ to $C_6$ cycloalkyl ring; and $R^{36}$ is selected from cycloalkyl, heterocycloalkyl, or aryl (e.g., phenyl); and provided that:

(1) when $R^{14}$ is selected from: group 6.0, 7.0, 7.1 or 8.0, and X is N, then $R^8$ is selected from: $C_3$ to $C_{10}$ alkyl, substituted $C_3$ to $C_{10}$ alkyl, arylalkyl, substituted arylalkyl, heteroarylalkyl, substituted heteroarylalkyl, cycloalkylalkyl, or substituted cycloalkylalkyl;

(2) when $R^{14}$ is selected from: group 6.0, 7.0, 7.1 or 8.0, and X is N, and $R^8$ is H, then the alkyl chain between $R^{13}$ (i.e., imidazole ring 2.0, 4.0 or 4.1) and the amide moiety (i.e., the —C(O)N$R^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cycloalkyl ring;

(3) when $R^{14}$ is group 5.0, and X is N, and $R^8$ is H, then the alkyl chain between $R^{13}$ (i.e., imidazole ring 2.0, 4.0 or 4.1) and the amide moiety (i.e., the —C(O)N$R^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cyloalkyl ring.

Preferred FPT inhibitors include peptides and peptidomimetic compounds and fused-ring tricyclic compounds of the above documents (which have already been incorporated herein by reference thereto). More preferred are the fused-ring tricyclic compounds, and most preferred are the compounds of WO 97/23478.

The FPT inhibition and anti-tumor activity of the compounds used as FPT inhibitors in this invention can be determined by methods known in the art—see, for example, the in vitro Enzyme Assays, Cell-Based Assays, Cell Mat Assays, and in vivo Anti-Tumor Studies in WO 95/10516 published Apr. 20, 1995, and the soft agar assay in WO 97/23478 published Jul. 3, 1997.

USE OF CHEMOTHERAPY AND/OR RADIATION THERAPY AS ADDITIONAL AGENTS IN THE TREATMENTS OF THE PRESENT INVENTION

Chemotherapeutic agents and/or radiation can optionally be added to treatment regimens of the present invention (in addition to the combination of (1) a farnesyl protein transferase (FPT) inhibitor, and (2) an additional Ras pathway signaling inhibitor). For use of chemotherapy and/or radiation therapy in combination with only an FPT inhibitor, reference can be made to Liu, M., et al. Cancer Res. 58:4947–4956 (1998) and U.S. patent application Ser. No. 09/217,335, now U.S. Pat. No. 6,096,757 expressly incorporated herein by reference.

Classes of compounds that can be used as the chemotherapeutic agent include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol®), Mithramycin, Deoxycoformycin, Mitomycin-C, L-Asparaginase, Interferons (especially IFN-α), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference.

PHARMACEUTICAL COMPOSITIONS

Inert, pharmaceutically acceptable carriers used for preparing pharmaceutical compositions of the FPT inhibitors and the Ras signaling pathway inhibitors described herein can be solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogenous mixture is then poured into conveniently sized molds, allowed to cool and thereby solidify.

Liquid preparations include solutions, suspensions and emulsions. As an examples may be mentioned water or water-propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The FPT inhibitors and the additional Ras pathway inhibitors described herein may also be deliverable transdermally. The transdermal compositions can take the form of creams, lotions, aerosols and/or emulsions and can be included in a transdermal patch of the matrix or reservoir type as are conventional in the art for this purpose.

Preferably the compounds are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.5 mg to 1000 mg, preferably from about 1 mg to 300 mg, more preferably 5 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the FPT inhibitors and the additional Ras pathway inhibitors will be regulated according to the judgment of the attending clinician (physician) considering such factors as age, condition and size of the patient as well as severity of the disease being treated. In general, dosage for an FPT inhibitor (when used as a single agent) can conceivably have an upper range of 2000 mg/day, preferably in a range of from 50 to 400 mg/day in cases where the FPT inhibitor is a fused-ring tricyclic benzocycloheptapyridine. However, in the combination therapy of the present invention, a preferred low dosage regimen of the FPT inhibitors is, e.g., oral administration of an amount in the range of from 1.4 to 400 mg/day, more preferably 1.4 to 350 mg/day, even more preferably 3.5 to 70 mg/day, preferably with a B.I.D. dosing schedule. A particularly low dosage range can be 1.4 to 70 mg/day.

The additional Ras pathway inhibitors can be administered according to therapeutic protocols well known in the art. See, e.g., Pegram, M. D., et.al. (1998). J Clin Oncol. 16:2659–2671. It will be apparent to those skilled in the art that the administration of the additional Ras pathway inhibitor can be varied depending on the disease being treated and the known effects of the additional Ras pathway inhibitor on that disease. Also, in accordance with the knowledge of the skilled clinician, the therapeutic protocols (e.g., dosage amounts and times of administration) can be varied in view of the observed effects of the administered therapeutic agents (i.e., additional Ras pathway inhibitor) on the patient, and in view of the observed responses of the disease to the administered therapeutic agents. In general, dosage for an additional Ras signaling pathway inhibitor (when used as a single agent) can be, e.g., in the range of 5 to 2000 mg/day. However, in the combination therapy of the present invention, a preferred low dosage regimen of an additional Ras signaling pathway inhibitor (e.g., a MEK inhibitor) is administration of an amount in the range of from 1 to 350 mg/day, more preferably 3.5 to 70 mg/day, preferably with a B.I.D. dosing schedule. A particularly low dosage range can be 1 to 70 mg/day.

Thus, in a preferred example of combination therapy in the treatment of cancers (e.g., pancreatic, lung or bladder cancer), the FPT inhibitor can be SCH 66336, as identified previously, administered orally in an amount of 70 mg/day, in two divided doses, on a continuous dosing regimen; and the additional Ras signaling pathway inhibitor can be PD098059 (or an analogue thereof) administered in an amount of 350 mg/day, in two divided doses, on a continuous dosing regimen.

In another preferred example of combination therapy in the treatment of cancers (e.g., pancreatic, lung or bladder cancer), the FPT inhibitor is SCH 66336, as identified previously, administered orally in an amount of 70 mg/day, in two divided doses, on a continuous dosing regimen; and the additional Ras signaling pathway inhibitor is U0126 (or an analogue thereof) administered in an amount of 350 mg/day, in two divided doses, on a continuous dosing regimen.

In the methods of this invention, an FPT inhibitor is administered concurrently or sequentially with an additional Ras pathway inhibitor. Thus, it is not necessary that, for example, the additional Ras pathway inhibitor and the FPT inhibitor should be administered simultaneously or essentially simultaneously. The advantage of a simultaneous or essentially simultaneous administration is well within the determination of the skilled clinician.

Also, in general, the FPT inhibitor and the additional Ras pathway inhibitor do not have to be administered in the same pharmaceutical composition, and may, because of different physical and chemical characteristics, have to be administered by different routes. For example, the FPT inhibitor may be administered orally to generate and maintain good blood levels thereof, while the additional Ras pathway inhibitor may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of FPT inhibitor and additional Ras pathway inhibitor will depend upon the diagnosis of the attending physicians and their judgement of the condition of the patient and the appropriate treatment protocol.

The FPT inhibitor and additional Ras pathway inhibitor may be administered concurrently (e.g., simultaneously, essentially simultaneously or within the same treatment protocol) or sequentially, depending upon the nature of the proliferative disease, the condition of the patient, and the actual choice of the additional Ras pathway inhibitor to be administered in conjunction (i.e., within a single treatment protocol) with the FPI inhibitor.

If the FPT inhibitor and additional Ras pathway inhibitor are not administered simultaneously or essentially simultaneously, then the initial order of administration of the FLIT inhibitor and additional Ras pathway inhibitor may not be important. Thus, the FPT inhibitor may be administered first followed by the administration of the additional Ras pathway inhibitor; or the additional Ras pathway inhibitor may be administered first followed by the administration of the FPT inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the additional Ras pathway inhibitor may be administered first, and then the treatment continued with the administration of the FPT inhibitor followed, where determined advantageous, by the administration of the additional Ras pathway inhibitor, and so on until the treatment protocol is complete.

Thus, in accordance with experience and knowledge, the practising physician can modify each protocol for the administration of a component (therapeutic agent—i.e., FPT inhibitor, additional Ras pathway inhibitor) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment. (Of course, as indicated previously, effective treatment using the methods of the present invention preferably results in a synergistic level of cancer cell death and/or tumor regression).

The following are examples (Examples 1–4) of capsule formulations for the FPT Inhibitory Compound:

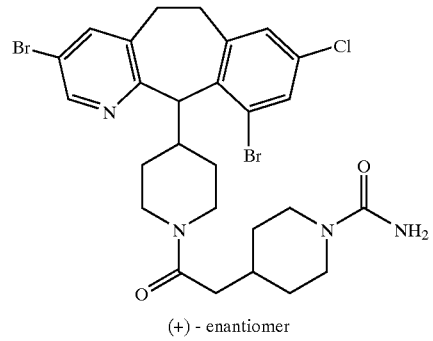

(+) - enantiomer

EXAMPLES 1 AND 2
Capsule Formulation

| Capsule Formulation | | | |
|---|---|---|---|
| Composition | Example 1 mg/capsule | Example 2 mg/capsule | % Composition |
| Solid Solution | 100 | 400.0 | 84.2 |
| Silicon Dioxide NF[1] | 0.625 | 2.5 | 0.5 |
| Magnesium Stearate NF[2] | 0.125 | 0.5 | 0.1 |
| Croscarmellose Sodium NF | 11.000 | 44.0 | 9.3 |
| Pluronic F68 NF | 6.250 | 25.0 | 5.3 |
| Silicon Dioxide NF[3] | 0.625 | 2.5 | 0.5 |
| Magnesium Stearate NF[4] | 0.125 | 0.5 | 0.1 |
| TOTAL | 118.750 | 475.00 | |
| Capsule size | No. 4 | No. 0 | |

Method (Examples 1 and 2)
Preparation of Solid Solution

| Preparation of Solid Solution | | |
|---|---|---|
| Composition | g/batch | % Composition |
| FPT Inhibitory Compound | 80 | 33.3 |
| Povidone NF K29/32 | 160 | 66.6 |
| Methylene Chloride | 5000 mL | evaporates |

Crystalline FPT Inhibitory Compound and the povidone were dissolved in methylene chloride. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearate[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. The mixture was encapsulated in hard shell gelatin capsule shells.

EXAMPLES 3 AND 4
Capsule Formulation

| Capsule Formulation | | | |
|---|---|---|---|
| Composition | Example 3 mg/capsule | Example 4 mg/capsule | % Composition |
| Solid Solution | 400 | 200.0 | 80.0 |
| Silicon Dioxide NF[1] | 3.75 | 1.875 | 0.75 |
| Magnesium Stearate NF[2] | 0.125 | 0.625 | 0.25 |
| Croscarmellose Sodium NF | 40.00 | 20.00 | 8.0 |
| Pluronic F68 NF | 50.00 | 25.00 | 10 |
| Silicon Dioxide NF[3] | 3.75 | 1.875 | 0.75 |
| Magnesium Stearate NF[4] | 1.25 | 0.625 | 0.25 |
| TOTAL | 500.00 | 250.00 | |
| Capsule size | No. 0 | No. 2 | |

Method (Examples 3 and 4)
Preparation of Solid Solution

| Preparation of Solid Solution | | |
|---|---|---|
| Composition | g/batch | % Composition |
| FPT Inhibitory Compound | 15 | 50 |
| Povidone NF K29/32 | 15 | 50 |
| Methylene Chloride | 140 mL | evaporates |
| Methanol | 60 mL | evaporates |

Crystalline FPT Inhibitory Compound and the povidone were dissolved in a mixture of methylene chloride and methanol. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearate[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. The mixture was encapsulated in hard shell gelatin capsule shells.

For information on formulations, reference can also be made to U.S. patent application Ser. Nos. 08/997168 and 60/068387 (filed Dec. 22, 1997), expressly incorporated herein by reference.

The scope of the invention in its pharmaceutical composition aspect is not to be limited by the examples provided.

All documents (e.g., publications and patent applications) cited herein are incorporated by reference to the same extent as if each individual document was specifically and individually indicated to be incorporated by reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

REFERENCES

Alessi, D. R., et.al. (1995). J Biol Chem. 270:27489–27494.

Barrington, R. E., et.al. (1998). Mol Cell Biol. 18:85–92.

Bishop, W. R., et.al. (1995). J Biol Chem. 270:30611–30618.

Campbell, S. L., et.al. (1998). Oncogene. 17:1395–1413.

Dengler, W. A., et.al. (1995). Anticancer Drugs. 6:522–32.

Duckworth, B. C., and Cantley, L. C. (1997). J Biol Chem. 272:27665–27670.

Dudley, D. T., et.al. (1995). Proc Natl Acad Sci USA. 92:7686–7689.

Favata, M. F., et.al. (1998). J Biol Chem. 273:18623–32.

Fry, D. W., et.al. (1994). Science. 9:1093–1095.

Goldstein, N. I., et.al. (1995). Clin Cancer Res. 1:1311–1318.

Gorczyca et al., (1993) Cancer Res. 53: 1945–51.

Graham, N. (1995). Exp Opin Ther Patents. 5:1269–1285.

Gutkind, J. S. (1998). J Biol Chem. 273:1839–1842.

Heldin, C. H. (1995). Cell. 80:213–23.

Hung, W. C., and Chaung, L. Y. (1998). Int J Oncol. 12:137–140.

James, G. L., et.al. (1994). J Biol Chem. 269:27705–27714.

Kohl, N., et.al. (1995). Nature Medicine. 1:792.

Kovalenko, M., et.al. (1994). Cancer Res. 54:6106–6114.

Lebowitz, P. F., et.al. (1997). J Biol Chem. 272:15591–15594.

Levitzki, A., and A. Gazit. (1995). Science. 267:1782–1788.

Liu, M., et.al. (1998). Cancer Res. 58:4947–4956.

Lowy, D. R., and Willumsen, B. (1993) Annu Rev Biochem. 62:851–8091.

Mendelsohn, J. (1992). J Nat'l Cancer Inst Monogr 13:125–131.

Moasser, M. M., et.al. (1998). Proc Natl Acad Sci. 95:1369–1374.

Monia, B. P., et.al. (1996). Nucleosides and Nucleotides Their Biological Applications-1. Supp 34.

Morrison, D. K., and Cutler, R. E. (1997). Curr Opin Cell Biol. 9:174–179.

Moyer, J. D., et.al. (1997). Cancer Res. 57:4838–4848.

Norgaard, P., et.al. (1999). Clin Cancer Res. 5:35–42.

Pegram, M. D., et.al. (1998). J Clin Oncol. 16:2659–2671.

Raff, M. (1998). Nature. 396:119–122.

Resnicoff, M. (1998). Int J Mol Med. 1:883–888.

Suzuki, N., et.al. (1998). Proc Natl Acad Sci USA. 95:15356–15361.

Thomberry, N. A. and Lazebnik, Y. (1998). Science. 281:1312–1316.

Trahey, M., and McCormick, F. (1987). Science. 238:542–5.

Wang, H. M., et.al. (1998). Anticancer Res. 18:2297–2300.

Whyte, D. B., et.al. (1997). J Biol Chem. 272:14459–14464.

Zhang, F. L., (1997). J Biol Chem. 272:10232–10239.

What is claimed is:

1. A method of treating cancer in a patient in need of such treatment, said treatment comprising administering, concurrently or sequentially, an effective amount of (1) the FPT inhibitor SCH 66336;

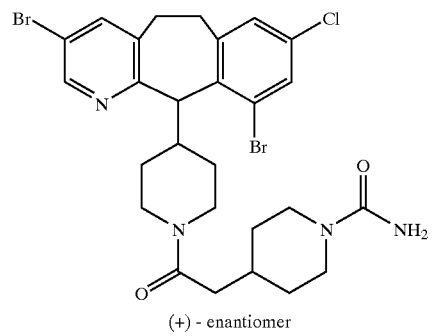

(+) - enantiomer and (2) the tyrosine kinase inhibitor STI-571;

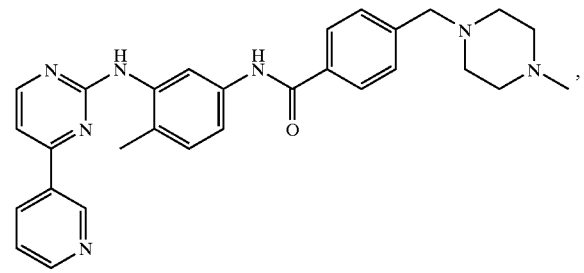

wherein the cancer is lung, selected from the group consisting of cancer, pancreatic cancer, colon cancer, ovarian cancer, liver cancers, myeloid leukemia, melanoma, thyroid follicular cancer, bladder carcinoma, glioma, myelodysplastic syndrome, breast cancer and prostate cancer.

2. The method according to claim 1, wherein SCH 66336 is administered in an amount of from 1.4 to 400 mg/day.

3. The method according to claim 2, wherein SCH 66336 is administered in an amount of from 3.5 to 70 mg/day.

4. A method of treating cancer in a patient in need of such treatment, said treatment comprising administering, concurrently or sequentially, an effective amount of (1) the FPT inhibitor SCH 66336;

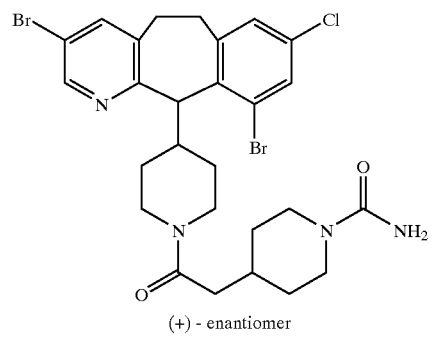

(+) - enantiomer and (2) the tyrosine kinase inhibitor STI-571;

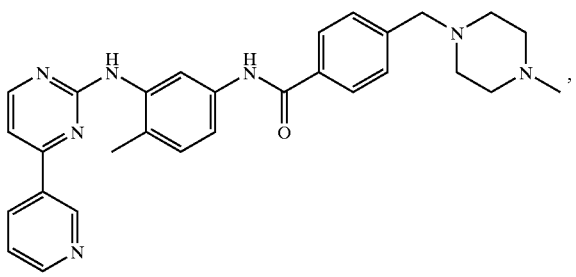

wherein the cancer is myeloid leukemia.

5. A method of treating cancer in a patient in need of such treatment, said treatment comprising administering, concurrently or sequentially, an effective amount of (1) the FPT inhibitor SCH 66336;

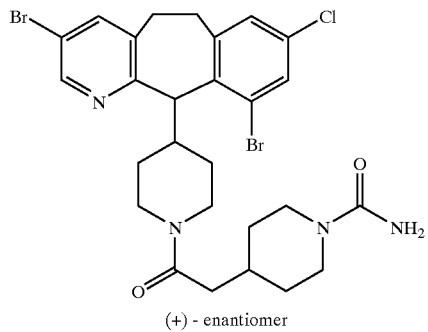

(+) - enantiomer and (2) the tyrosine kinase inhibitor STI-571;

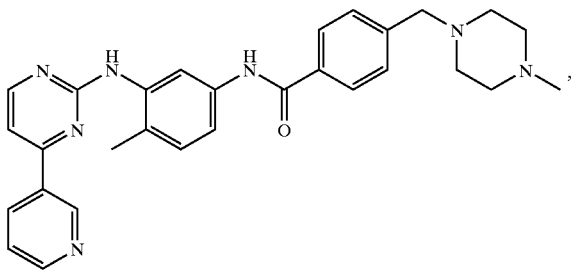

wherein the cancer is myelodysplastic syndrome.

6. A method of treating cancer in a patient in need of such treatment, said treatment comprising administering, concurrently or sequentially, an effective amount of (1) the FPT inhibitor SCH 66336;

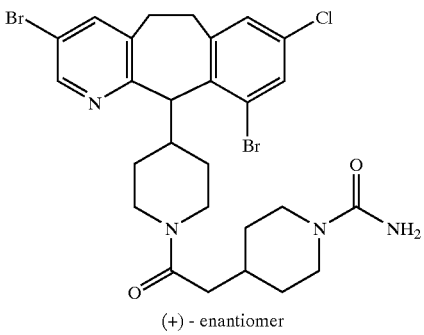

(+) - enantiomer and (2) the tyrosine kinase inhibitor STI-571;

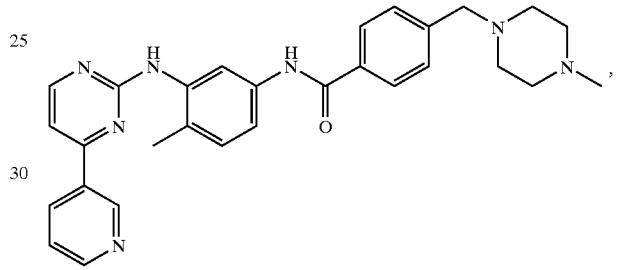

wherein the cancer is selected from the group consisting of melanoma, myeloid leukemias, sarcomas, thyroid follicular cancer and myelodysplastic syndrome.

* * * * *